United States Patent
Saydam et al.

(10) Patent No.: US 9,879,254 B2
(45) Date of Patent: Jan. 30, 2018

(54) TARGETING RNAS TO MICROVESICLES

(71) Applicant: THE GENERAL HOSPITAL CORPORATION, Boston, MA (US)

(72) Inventors: Okay Saydam, Vienna (AT); Mehmet Fatih Bolukbasi, Worcester, MA (US); Arda Mizrak, San Francisco, CA (US); Xandra O. Breakefield, Newton, MA (US)

(73) Assignee: THE GENERAL HOSPTIAL CORPORATION, Boston, MA (US)

( * ) Notice: Subject to any disclaimer, the term of this patent is extended or adjusted under 35 U.S.C. 154(b) by 24 days.

(21) Appl. No.: 14/372,640

(22) PCT Filed: Jan. 17, 2013

(86) PCT No.: PCT/US2013/021879
§ 371 (c)(1),
(2) Date: Jul. 16, 2014

(87) PCT Pub. No.: WO2013/109713
PCT Pub. Date: Jul. 25, 2013

(65) Prior Publication Data
US 2015/0024036 A1    Jan. 22, 2015

Related U.S. Application Data

(60) Provisional application No. 61/587,995, filed on Jan. 18, 2012.

(51) Int. Cl.
| | |
|---|---|
| *C12N 15/10* | (2006.01) |
| *C12N 15/113* | (2010.01) |
| *C12N 15/09* | (2006.01) |
| *C12N 15/63* | (2006.01) |
| *C12N 15/88* | (2006.01) |
| *C12N 15/86* | (2006.01) |
| *C12N 15/11* | (2006.01) |

(52) U.S. Cl.
CPC ............ *C12N 15/113* (2013.01); *C12N 15/63* (2013.01); *C12N 15/86* (2013.01); *C12N 15/88* (2013.01); *C12N 15/111* (2013.01); *C12N 2310/141* (2013.01); *C12N 2310/3519* (2013.01); *C12N 2320/32* (2013.01)

(58) Field of Classification Search
None
See application file for complete search history.

(56) References Cited

U.S. PATENT DOCUMENTS

| | | |
|---|---|---|
| 6,287,788 B1 | 9/2001 | Bard et al. |
| 2004/0241176 A1 | 12/2004 | Lamparski |
| 2010/0203529 A1 | 8/2010 | Kuslich et al. |
| 2011/0268750 A1 | 11/2011 | Mamoun |

FOREIGN PATENT DOCUMENTS

WO    2008112127 A2    12/2009

OTHER PUBLICATIONS

Invitrogen product information for pcDNA6/His A, B, and C, Catalog No. V222-20, Version B, (2000) retrieved from http://users.auth.gr/~pchristo/research/plasmids/com/pcDNA°/0206_His%020A,B,C.pdf on Mar. 3, 2016).*
Mfold Web Server RNA folding form, downloaded from http://unafold.rna.albany.edu/?q=mfold/RNA-Folding-Form on Oct. 19, 2016.*
Hung et al., "A platform for actively loading cargo RNA to elucidate limiting steps in EV-mediated delivery", J. Extracell. Vesicles 5:31027 (2016).
Shen et al., "Protein Targeting to Exosomes/Microvesicles by Plasma Membrane Anchors", J. Biol. Chem. 286 (16):14383-14395 (2011).
Villarroya-Beltri et al., "Sumoylated hnRNPA2B1 controls the sorting of miRNAs into exosomes through binding to specific motifs", Nat. Commun. 4:2980 (2013).
Yang et al., "The cis-acting signals that target proteins to exosomes and microvesicles", Biochem. Soc. Trans. 41:277-282 (2013).
Andreassi et al., "To localize or not to localize: mRNA fate is in 3'UTR ends", Trends Cell Biol 19(9) 465-474 (2009).
Bartel, "MicroRNAs: genomics, biogenesis, mechanism, and function", Cell 116(2) 281-297 (2004).
Berger et al., "Galanin and galanin receptors in human cancers", Neuropeptides 39(3) 353-359 (2005).
Fabian et al., "Regulation of mRNA translation and stability by microRNAs", Annu Rev Biochem 79: 351-379 (2010).
Gan et al., "Identification of an inhibitory budding signal that blocks the release of HIV particles and exosome/microvesicle proteins", Mol Biol Cell 22(6) 817-830 (2011).
Garneau et al., "The highways and byways of mRNA decay", Nat Rev Mol Cell Biol 8(2) 113-126 (2007).

(Continued)

*Primary Examiner* — Richard A Schnizer
(74) *Attorney, Agent, or Firm* — Nixon Peabody LLP; David S. Resnick; Shayne Y. Huff

(57) ABSTRACT

Disclosed herein is an isolated nucleic acid molecule comprising a first nucleic acid sequence 5'-ACCCTGCCGC-CTGGACTCCGCCTGT-3' (SEQ ID NO: 22), or a functional variant thereof, operably linked to a second, heterologous nucleic acid sequence. The isolated nucleic acid molecule can be DNA (in an expression vector) and RNA (mRNA, shRNA, orncRNA). Also disclosed is a microvesicle comprising the nucleic acid molecule and a microvesicle preparation comprising the microvesicle. Also disclosed is an in vitro method of producing a microvesicle preparation enriched for a specific RNA sequence by transfecting cells with the nucleic acid sequence, and isolating microvesicles generated therefrom. Methods of delivering therapeutic RNA to a subject are also disclosed.

12 Claims, 18 Drawing Sheets

(56) References Cited

OTHER PUBLICATIONS

Gibbings et al., "Multivesicular bodies associate with components of miRNA effector complexes and modulate miRNA activity", Nat Cell Biol 11(9) 1143-1149 (2009).
Jansen et al., "mRNA localization: message on the move", Nat Rev Mol Cell Biol 2(4) 247-256 (2001).
Kadomatsu, "The midkine family in cancer, inflammation and neural development", Nagoya J Med Sci 67(3-4) 71-82 2005).
Kislauski et al., "Isoform-specific 3'-untranslated sequences sort alpha-cardiac and beta-cytoplasmic actin messenger RNAs to different cytoplasmic compartments", J Cell Biol 123(1) 165-172 (1993).
Kislauski et al., "Sequences responsible for intracellular localization of beta-actin messenger RNA also affect cell phenotype", J Cell Biol 127(2) 441-451 (1994).
Liu et al., "MicroRNA-dependent localization of targeted mRNAs to mammalian P-bodies", Nat Cell Biol 7(7) 719-723 (2005).
Martin et al., "mRNA localization: gene expression in the spatial dimension", Cell 136(4) 719-730 (2009).
Meignin et al., "Transmitting the message: intracellular mRNA localization", Curr Opin Cell Biol 22(1) 112-119 (2010).
Montgomery et al., "Splicing and dicing with a SERRATEd edge", Proc Natl Arad Sci USA 105(25) 8489-8490 (2008).
Ross et al. "Characterization of a beta-actin mRNA zipcode-binding protein", Mol Cell Biol 17(4) 2158-2165 (1997).

\* cited by examiner

FIG. 1

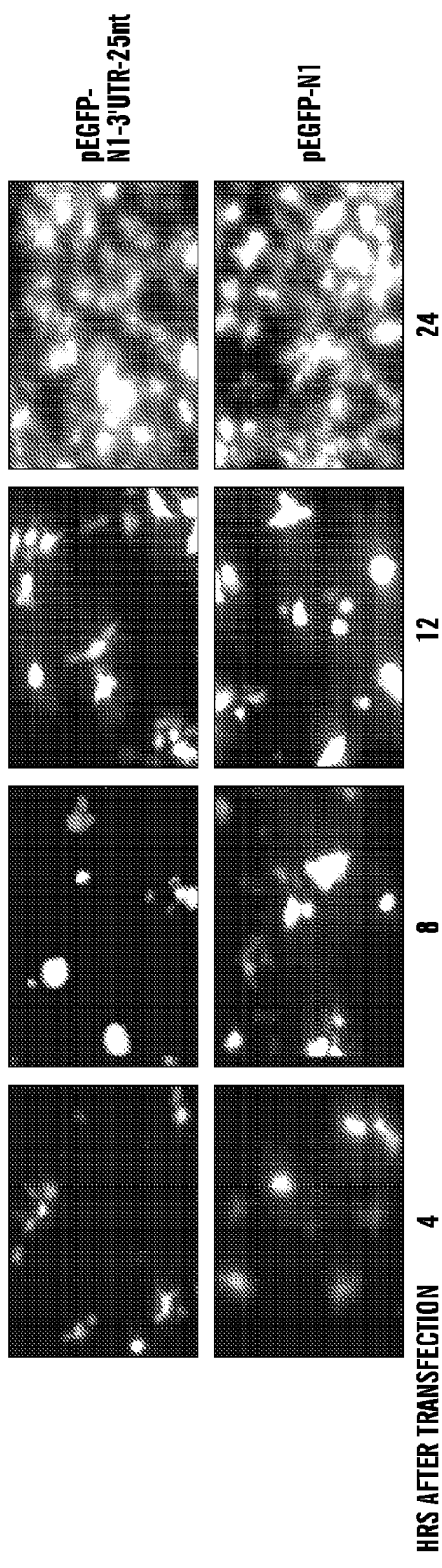
FIG. 3B
FIG. 3C

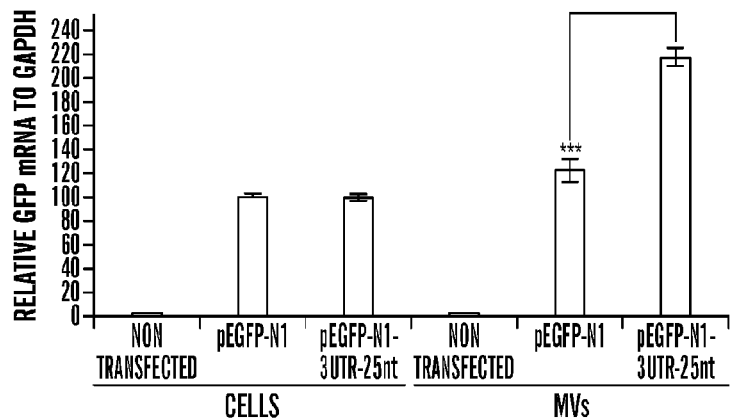
*FIG. 4A*
```
                        Cells                              MVs
pEGFP-N1-3UTR-25nt:      ACC[CTGCC]GCCTGGACTCCGCCTGT (SEQ ID NO: 79)
                            * * * * *
pEGFP-N1-3UTR-25nt-MT1:  ACCGCATGGCCTGGACTCCGCCTGT (SEQ ID NO: 80)
                            * * * * *
pEGFP-N1-3UTR-25nt-MT2:  ACCACTTAGCCTGGACTCCGCCTGT (SEQ ID NO: 81)
```
*FIG. 4B*
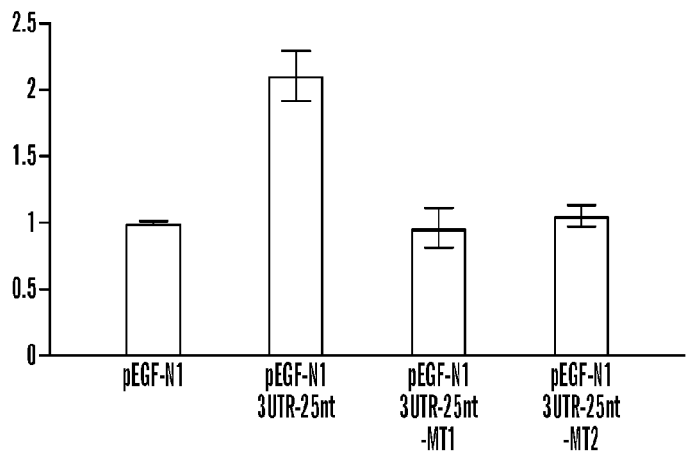
*FIG. 4C* pEGFP-N1-3UTR-25nt    ACCCTGCCGCCTGGACTCCGCCTGT (SEQ ID NO: 82)
pEGFP-N1-3UTR-25nt-MT3  ACCCTGCCGCCTGGATCAAGCCTGT (SEQ ID NO: 83)
pEGFP-N1-3UTR-25nt-MT4  ACCCTGCCGCCCTGATCGCGCCTGT (SEQ ID NO: 84)
*FIG. 5A*
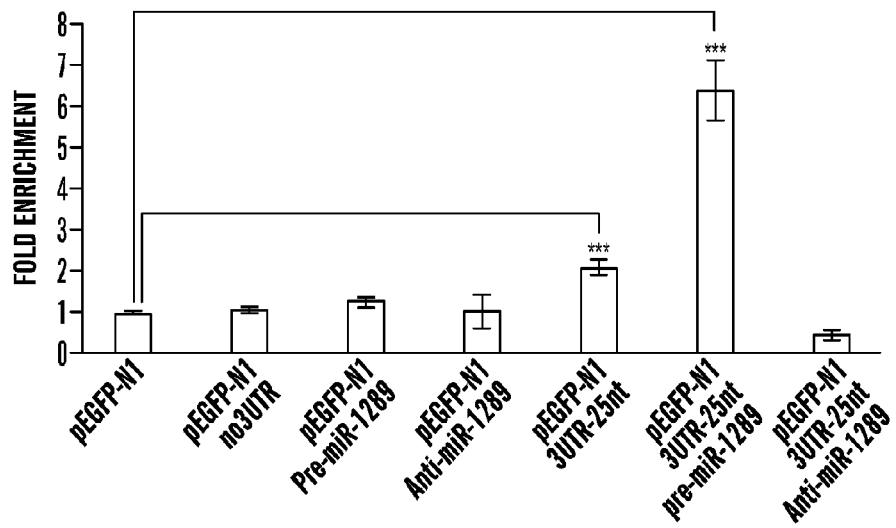
*FIG. 5B*
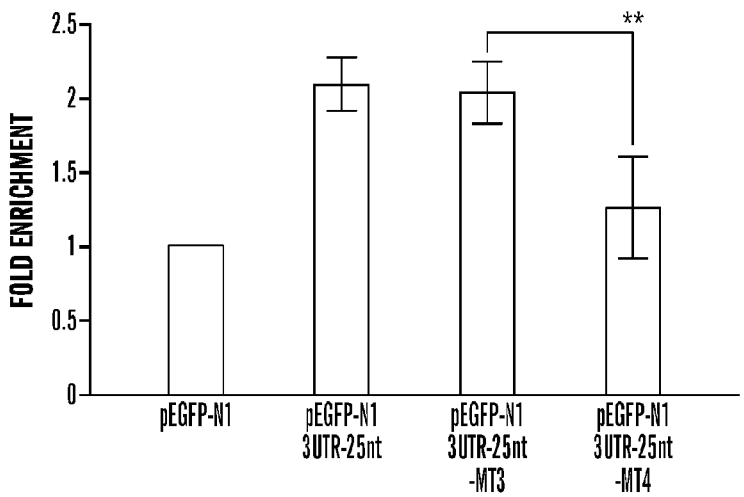
*FIG. 5C*

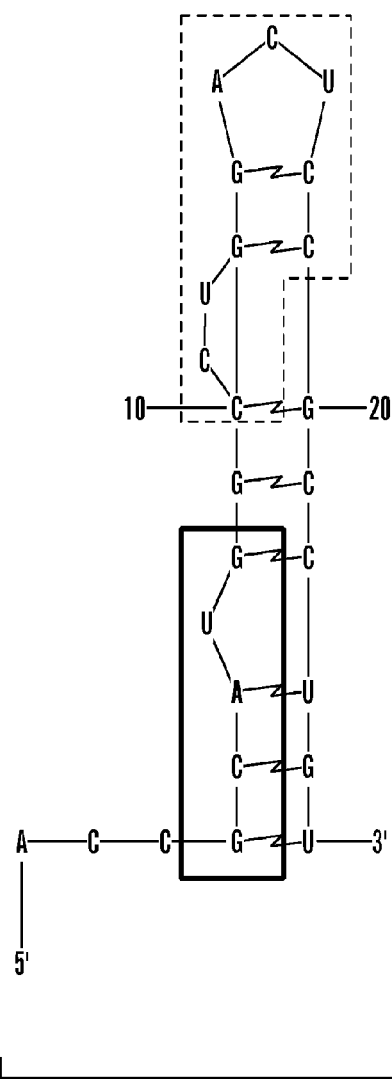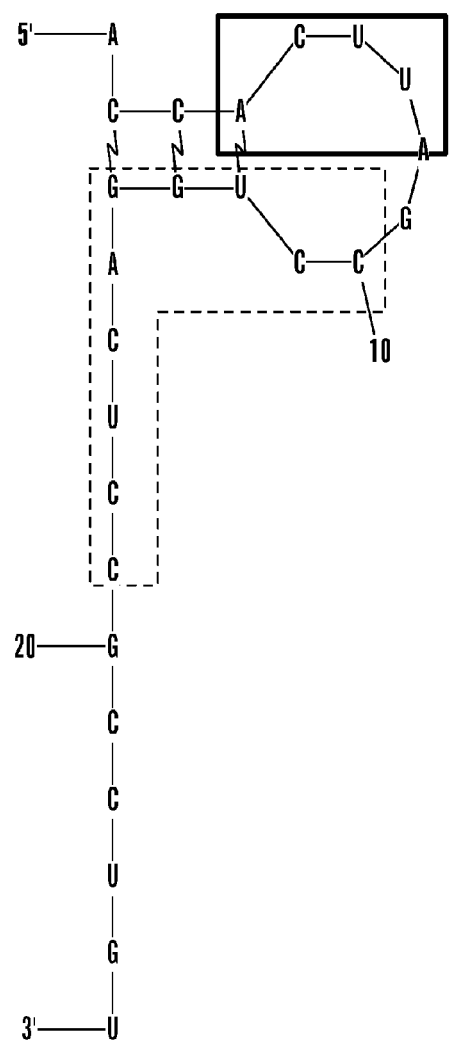
FIG. 8 pEGFP-N1

5'-GCGGGCCGGGACTCTAGATCATATAATCAGCCATATACCACATTTGTAGAGGTTTTACTTGCTTTAAAAAACCTCCCACACCTCCCCCTGAACCTGAAACATAAAATGAATGCAATTGTTGTTAACTTGTTTATTGCAGCTTATAATGGTTACAAATAAAGCAATAGCATCACAAATTTCACAAATAAAGCATTTTTTTCACTGCATTCTAGTTGTGTGGTTTGTCCAAACTCATCAATGTATCTTAAG-3' (SEQ ID NO: 85)

pEGFP-N1-3UTR-25nt

5'-GCGGCCGCGACCCTGCCGCTGACTCCGCCTGTACAAATAAAGCAATAGCATCACAAATTTCACAAATAAAGCATTTTTTTCACTGCCTTAAG-3' (SEQ ID NO: 86)

pEGFP-N1-3UTR-25nt-MT1

5'-GCGGGCCGGACCGCCATGGCCTGGACTCCGCCTGTACAAATAAAGCAATAGCATCACAAATTTCACAAATAAAGCATTTTTTTCACTGCCTTAAG-3' (SEQ ID NO: 87)

FIG. 10 pEGFP-N1-3UTR-25nt-MT2
5'-GCGGCCCGACCACTTAGCCTGGACTCCGGCCTGTACAAATAAAGCAATAGCATCACAAATTTCACAAATAAAGCATTTTTTCACTGCCTTAAG-3'
(SEQ ID NO: 88)

pEGFP-N1-3UTR-25nt-MT3
5'-GCGGCCCGACCCTGCCCGGCCTGATCAAGCCTGTACAAATAAAGCAATAGCATCACAAATTTCACAAATAAAGCATTTTTTCACTGCCTTAAG-3'
(SEQ ID NO: 89)

pEGFP-N1-3UTR-25nt-MT4
5'-GCGGCCCGACCCTGCCCGGCCCTGATCGGCGGCCTGTACAAATAAAGCAATAGCATCACAAATTTCACAAATAAAGCATTTTTTCACTGCCTTAAG-3'
(SEQ ID NO: 90)

*FIG. 10 (cont.)*

NM_003614.1      5'-ACCUGCGCCUGGACUCCG-3'
                    |..|.|.|||||||||
hsa-miR1289      3'-UUUUACGUCUAAGGACCUGAGGU-5'

NM_031309.4      5'-UGAGU-UAGGCCUUUUGACUCCA-3'
                    .|.|||.|.|||.|||||||
hsa-miR1289      3'-UUUUACGUCUAAGGACCUGAGGU-5'

NM_001702.2      5'-AGGCCGAACGUGCCUCAGACUCCG-3'
                    .|.||.|.|||.||||||||
hsa-miR1289      3'-UUUUACGUCUAAGGA-CCUGAGGU-5'

NM_001080547.1   5'-CUUCGGCCUCCCAGGACUCCA-3'
                    .||.|||.|||.||||||||
hsa-miR1289      3'-UUUUACGUCUAAGGACCUGAGGU-5'

NM_001001712.2   5'-UUCAUGAAUAUU-CAUGACUCCU-3'
                    ..|||.|..|.|.|||||||
hsa-miR1289      3'-UUUUACGUCUAAGGACCUGAGGU-5'

NM_005764.3      5'-GUGGCUCCAACCCAAGACUCCC-3'
                    ....||.|.|.|||||||||
hsa-miR1289      3'-UUUUACGUCUAAGGACCUGAGGU-5'

XM_928353.1      5'-CCAGGAGGCCUGCUGACUCCAC-3'
                    .|......|.|.||||||||.
hsa-miR1289      3'-UUUUACGUCUAAGGACCUGAGGU-5'

NM_012272.1      5'-GUCCCCUACUCCCUGGACUAGU-3'
                    .....|.|...|||||||||
hsa-miR1289      3'-UUUUACGUCUAAGGACCUGAGGU-5'

*FIG. 11*

NM_032192.2      5'-UUUCCCUUCUUCCUGACUCCA-3'
                       :||::|::|||||||||||
hsa-miR1289      3'-UUUUACGUCUAAGGACCUGAGGU-5'

NM_001013635.2   5'-GGGUCAGGCAGAGAGACUCCC-3'
                       ||||:||:||||||||:.
hsa-miR1289      3'-UUUUACGUCUAAGGACCUGAGGU-5'

NM_152795.2      5'-UCCUCACUCAAGAUCUGACUCCA-3'
                    :|::|::|||:|:|||||||||
hsa-miR1289      3'-UUUUACGUCUAAGGACCUGAGGU-5'

NM_199165.1      5'-   CUGGCCAGGCGUCUGGACUUGU-3'
                       ::||::|:||::||||||||:...
hsa-miR1289      3'-UUUUACGUCUAAGGACCUGAGGU-5'

NM_198576.2      5'-CUGCCCAGCCACCUGGACGUGA-3'
                    :..:||||:||||||||::..|
hsa-miR1289      3'-UUUUACGUCUAAGGACCUGAGGU-5'

NM_181553.2      5'-UUGGAGCGGAGCCUGGACUUCU-3'
                    ::||:||:|:||||||||:..|
hsa-miR1289      3'-UUUUACGUCUAAGGACCUGAGGU-5'

FIG. 11 (cont.)

TARGETING RNAS TO MICROVESICLES

CROSS REFERENCE TO RELATED APPLICATIONS

This Application is a 35 U.S.C. § 371 National Phase Entry Application of International Application No. PCT/US2013/021879 filed Jan. 17, 2013, which designates the U.S., and which claims the benefit under 35 U.S.C. § 119(e) of U.S. Provisional Application No. 61/587,995, filed Jan. 18, 2012, the contents of each of which are incorporated herein by reference in their entireties.

GOVERNMENT SUPPORT

This invention was made with government support under Grant Numbers NS037409, NS024279, and CA141150 awarded by the National Institutes of Health (NIH). The Government has certain rights in this invention.

SEQUENCE LISTING

The instant application contains a Sequence Listing which has been submitted electronically in ASCII format and is hereby incorporated by reference in its entirety. Said ASCII copy, created on May 17, 2017, is named 030258-071952-US SL.txt and is 18,676 bytes in size.

FIELD OF THE INVENTION

The invention relates to the field of intracellular molecular trafficking and therapeutic administration of nucleic acid sequences.

BACKGROUND OF THE INVENTION

Membrane-derived microvesicles (MVs) include a range of extracellular vesicles, including exosomes, microparticles and shed MVs secreted by many cell types under both normal physiological and pathological conditions [1]. As intercellular communication tools, MVs have been reported to have roles in a wide range of cellular functions: immunological modulation, coagulation, and tumor progression, including angiogenesis and metastasis [2,3]. Additionally, they have been reported to serve as vehicles for transferring cargo (mRNA, miRNA, non-coding RNAs, proteins and oncogenes) between cells [4-8]. The mRNA content in MVs opens new research opportunities from cancer diagnostics to gene therapy applications [9-12]. Despite the intensive research in analyzing the RNA content of MVs, it remains unclear how RNAs are directed to MVs.

Mechanistically, cis-acting regulatory sequences and trans-acting proteins are considered as the main driving forces of mRNA localization within cells and have an important role in post-transcriptional regulation. Such sequences, also known as zip codes, are typically found in the 3'-untranslated regions (3' UTRs) of mRNA transcripts and mediate binding of a ribonuclear protein complex to the mRNA which temporarily blocks its translation and mediates movement via the cytoskeleton to a cellular location where it releases the mRNA and translation commences [13,14].

In addition to zip codes, microRNAs (miRNAs) also have a critical role in post-transcriptional regulation of mRNAs. miRNAs are small, non-coding, single-stranded RNA molecules [~21-23 nucleotides (nt) long] that regulate levels of gene expression in many organisms [15]. miRNAs mediate post-transcriptional regulation in three ways, by mRNA degradation, mRNA destabilization via deadenylation and translational repression [16]. In addition to negative regulation, miRNAs have also been reported to function in the activation of translation in some cases [17]. Although zip codes and miRNA target sequences are both found in the 3'UTRs of the mRNA transcripts, there has been no report of cooperation between these two regulatory mechanisms in mRNA fate.

SUMMARY OF THE INVENTION

One aspect of the invention is an isolated nucleic acid molecule comprising a first nucleic acid sequence 5'-ACCCTGCCGCCTGGACTCCGCCTGT-3' (SEQ ID NO: 22), or a functional variant thereof, operably linked to a second, heterologous nucleic acid sequence. In one embodiment, the isolated nucleic acid molecule is DNA or RNA. In one embodiment, the nucleic acid molecule is DNA and the DNA is in the context of an expression vector. In one embodiment, the nucleic acid molecule is RNA and the RNA is selected from the group consisting of mRNA, shRNA, and ncRNA. In one embodiment, the first nucleic acid sequence is located 3' of the second nucleic acid sequence. In one embodiment, the nucleic acid molecule is DNA and the first nucleic acid sequence is located 5' of a poly adenylation site (DNA). In one embodiment, the nucleic acid molecule is RNA and the first nucleic acid sequence is located 5' of a poly adenylation sequence.

Another aspect of the invention is a microvesicle comprising a RNA molecule comprising a first nucleic acid sequence 5'-ACCCTGCCGCCTGGACTCCGCCTGT-3' (SEQ ID NO: 22), or a functional variant thereof, operably linked to a second heterologous nucleic acid sequence. In one embodiment, the RNA molecule is selected from the group consisting of mRNA, shRNA, and ncRNA. In one embodiment, the first nucleic acid sequence is located 3' of the second nucleic acid sequence. In one embodiment, the first nucleic acid sequence is located 5' of a poly A sequence.

Another aspect of the invention is an in vitro microvesicle preparation comprising a microvesicle described herein.

Another aspect of the invention is an in vitro method of producing a microvesicle preparation enriched for a specific RNA sequence, comprising transfecting cells in vitro with a DNA molecule in expressible form, comprising a first nucleic acid sequence 5'-ACCCTGCCGCCTGGACTCGCCTGT-3' (SEQ ID NO: 22), or a functional variant thereof, operably linked to a second, heterologous nucleic acid sequence, under conditions suitable for expression, and isolating microvesicles generated by the transfected cells, to thereby produce a microvesicle preparation enriched for the specific RNA sequence. In one embodiment, the method further comprises transfecting the cells with a pre-miR-1289 in expressible form under conditions suitable for expression. In one embodiment, the specific RNA sequence is selected from the group consisting of a mRNA, a shRNA, and a regulatory ncRNA. In one embodiment, transfection is by lipofection. In one embodiment, the cells are primary cells. In one embodiment, the cells are dendritic cells.

Another aspect of the invention is a method of delivering a therapeutic RNA to a subject, comprising, administering to the subject a microvesicle preparation enriched for the therapeutic RNA sequence, generated by the method described herein. In one embodiment, administration is systemic (e.g., via injection). In one embodiment administering is by local delivery to a site of target tissue. In one embodiment, administering is by injection into a tumor. In one embodiment, the therapeutic RNA is selected from the group consisting of a pre-miR, a non-coding regulatory RNA, a coding mRNA, and combinations thereof.

Another aspect of the invention is a method of delivering a therapeutic molecule to a subject, comprising delivering to cells of the subject a DNA molecule in expressible form, comprising a first nucleic acid sequence 5'-ACCCTGC-CGCCTGGACTCCGCCTGT-3' (SEQ ID NO: 22), or a functional variant thereof, operably linked to a second, heterologous nucleic acid sequence, under conditions suitable for expression. In one embodiment, the DNA molecule further comprises a pre-miR, e.g., pre-miR-1289, in expressible form. In one embodiment, the DNA molecule is in the context of a viral expression vector.

Another aspect of the invention is a method of inhibiting incorporation of RNA into microvesicles by a cell comprising, inhibiting of an endogenous miR, e.g., miR-1289, in the cell, to thereby inhibit RNA incorporation into microvesicles by the cell. In one embodiment, inhibiting endogenous miR-1289 is by transfection with an anti-miR-1289 sequence.

Definitions

"Microvesicles", as the term is used herein, refers to membrane-derived microvesicles, which includes a range of extracellular vesicles, including exosomes, microparticles and shed microvesicles secreted by many cell types under both normal physiological and pathological conditions. The methods and compositions described herein can be applied to microvesicles of all sizes; preferably 30 to 800 nm; and more preferably 30 to 200 nm.

The term "heterologous" is used herein to describe the relationship of one nucleic acid sequence to one or more different nucleic acid sequences. The term heterologous, in reference to two or more such nucleic acid sequence, indicates that the different nucleic acid sequences are found in nature within separate, different and distinct larger nucleic acids. The joining of heterologous nucleic acid sequences creates a non-naturally occurring juxtaposition of sequences. Such joining is the product of engineering performed in the laboratory.

The term "isolated" when used in reference to a nucleic acid sequence refers to the fact that the nucleic acid sequence is removed from the context of other nucleic acid sequences in which it is present in nature (e.g., in the context of a chromosome). The nucleic acids of the invention are typically present in isolated form.

The terms "patient", "subject" and "individual" are used interchangeably herein, and refer to an animal, particularly a human, to whom treatment including prophylaxic treatment is provided. This includes human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. "Mammal" refers to any animal classified as a mammal, including humans, non-human primates, domestic and farm animals, and zoo, sports, or pet animals, such as dogs, cats, cattle, horses, sheep, pigs, goats, rabbits, etc.

The term "operably linked" is used herein to refer to a functional relationship of one nucleic acid sequence to another nucleic acid sequence. Nucleic acid sequences are "operably linked" when placed into a functional relationship with one another. For example, a promoter or enhancer is operably linked to a coding sequence if it affects the transcription of the sequence; or a ribosome binding site is operably linked to a coding sequence if it is positioned so as to facilitate translation. The DNA sequences being linked may be contiguous, or separated by intervening sequences, and when necessary in the same reading phase and/or appropriate orientation. Linking is accomplished, for example, by ligation at convenient restriction sites. If such sites do not exist, the synthetic oligonucleotide adaptors or linkers are used in accordance with conventional practice.

The term "target nucleic acid molecule" or "target RNA" is used herein to refer to a nucleic acid molecule that is specifically engineered to be enriched in microvesicles produced by a cell in which it is expressed, by the methods described herein.

The term "in expressible form" when used in the context of a DNA molecule means located within functional distance of sequences necessary for transcription of the DNA into RNA by the RNA polymerase transcription machinery found in eukaryotic cells (e.g., promoter sequences, and other 5' regulatory sequences). One example is a DNA molecule in the context of an expression vector. Expression can refer to transcription of DNA into RNA, and when protein coding sequences are involved, expression may also encompass translation of the mRNA into protein.

As the term is used herein, "transfection" refers to the introduction of nucleic acid into a cell (e.g., for the purpose of expression of the nucleic acid by the cell). Examples of methods of transfection are electroporation, calcium phosphate, lipofection, and viral infection utilizing a viral vector. Typically nucleic acid is introduced into a cell in expressible form. That means that the nucleic acid is in the appropriate context of regulatory sequences such that the cellular machinery will recognize it and process it (e.g., transcribe RNA from DNA, translate protein from RNA). In one embodiment, a nucleic acid is in expressible form when it is inserted into an expression vector in the proper orientation to confer expression.

An "effective amount" as the term is used herein, is used to refer to an amount that is sufficient to produce at least a detectable amount of the desired results. An effective amount will vary with the specific conditions and circumstances. Such an amount can be determined by the skilled practitioner for a given situation.

BRIEF DESCRIPTION OF THE DRAWINGS

FIG. 1 shows alignment of the 3' UTRs of the top 20 enriched transcripts identified by the experiments described herein. 3' UTR sequences of the top 20 enriched transcripts were obtained from NCBI and Ensemble databases. The sequences were aligned with ClustalW a multiple sequence alignment program. The 25 nt sequence used in this study and referred as the zip code is shown in the red rectangle.

FIG. 3A-FIG. 3C shows experimental results in the form of a bar graph, photographs of cells examined under fluorescence microscope, and photographs of a Western Blot. The results indicate that the EGFP mRNA with the zip code in the 3' UTR is stable and translated. HEK-293T cells were transfected either with pEGFP-N1 or pEGFP-N1-3UTR-25nt plasmids. FIG. 3A) Total RNA was isolated at the indicated time points and qRT-PCR was performed for EGFP and GAPDH mRNAs. EGFP mRNA levels were normalized to GAPDH mRNA. FIG. 3B) Under the same experimental condition, cells were examined under fluorescence microscope for EGFP expression at the same time points (20× magnification). FIG. 3C) HEK-293T cells were transfected as above and Western blot analysis was performed with antibodies to EGFP and β-actin. pEGFP-N1 (lane 1 and 2) and pEGFP-N1-3UTR-25nt (lane 3 and 4).

FIG. 4A-FIG. 4C show experimental results in the form of bar graphs, and also specific nucleic acid sequences used in the experiments. The results indicate the functionality of the zip code in the transfer of messages into microvesicles. FIG. 4A) HEK-293T cells were non-transfected or transfected with either wild-type EGFP expressing plasmids, pEGFP-N1-3UTR-WT or pEGFP-N1-3UTR-25nt. Seventy-two hours later, total RNA was isolated from cells and MVs, and qRT-PCR were performed for EGFP and GAPDH mRNAs. The data were normalized to the level of GAPDH mRNA in each sample. GAPDH mRNA levels were similar in cells transfected with either construct, as well as in the MVs derived from them. Five independent experiments were performed in triplicate and the values are expressed as mean+/−S.D. using Student's t-test; ***=p<0.001. FIG. 4B) Mutated sequences in the zip code are shown for MT1 and MT2 constructs. FIG. 4C) Similar MV enrichment experiments were performed as in a) using the wild-type and mutated constructs shown in FIG. 4B).

FIG. 5A-FIG. 5E show experimental results in the form of bar graphs, and also specific nucleic acid sequences used in the experiments. The results indicate the effect of miRNA-1289 on EGFP mRNA enrichment within microvesicles. FIG. 5A) miR-1289 binding site in yellow highlighted region (13 nt) and mutations in asterisks in the zip code are shown for MT3 and MT4. FIG. 5B) HEK-293T cells were transfected with indicated EGFP expressing plasmids or co-transfected with plasmids and/or pre or anti-miR-1289. Seventy-two hours later, total RNA was isolated from cells and MVs and qRT-PCR were performed for EGFP and GAPDH mRNAs. The data were normalized to the level of GAPDH mRNA in each sample and presented as fold enrichment in MVs. Microsomal EGFP mRNA enrichment is shown according to the EGFP/GAPDH ratios of pEGFP-N1, pEGFP-N1no 3' UTR, pEGFP-N1+premiR-1289, pEGFP-N1+anti-miR-1289, pEGFP-N1-3UTR-25nt, pEGFP-N1-3UTR-25nt+premiR-1289, pEGFP-N1-3UTR-25nt+anti-miR-1289. Student's t-test, =p<0.01. FIG. 5C) Similar transfection and qRT-PCR reactions were performed as in B) including the mutated plasmids: pEGFP-N1-3UTR-25nt-MT3 and pEGFP-N1-3UTR-25nt-MT4. EGFP mRNA enrichment in MVs is shown using normalized values. FIG. 5D) pMiR-Report vectors containing the pMir-zip code wild-type 25 nt or mt miR-1289 (MT4) binding sites in the 3'UTR were co-transfected into HEK-293T cells together with pre-miR-1289 or pre-control 1, as well as an expression cassette for Rluc. Two days later, Fluc activity in the cells was measured and normalized to Rluc activity. Five independent experiments were performed in triplicate and the values are expressed as mean+/−S.D. Student's t-test, *=p<0.001. FIG. 5E) Primary GBM cells were transfected either with pre-miR-1289 or pre control 1 and 72 h later, MVs were collected as above and qRT-PCR was performed for GALR3, MDK, and GAPDH mRNAs. This experiment was performed in triplicate and the data were normalized to the level of GAPDH mRNA in each sample and presented as fold enrichment MVs/cell. The values are expressed as mean+/−S.D. Student's t-test, ***=p<0.001.

FIG. 6A) HEK-293T cells were transfected overnight with pEGFP-N1 and other derived plasmids. Twelve hours later transfection medium was replaced (t=0 h). At different time points, total RNA was extracted and qRT-PCR was performed for EGFP and GAPDH mRNAs. EGFP mRNA levels were normalized to GAPDH mRNA. For each plasmid, EGFP mRNA level at t=0 is taken as 1 and other levels at different time points are normalized accordingly. FIG. 6B) HEK-293T cells were transfected with pEGFP-N1 or pEGFP-N1-3UTR-25nt alone or with pre/anti control (CT) or pre/anti-miR-1289. Seventy-two h after transfection cells were harvested and Western blot analysis was performed with antibodies to EGFP and β-actin. FIG. 6C) In parallel experiments, total RNA was isolated and qRT-PCR was performed using EGFP and GAPDH primers. EGFP mRNA levels were normalized to GAPDH mRNA.

FIG. 7 discloses the RNA version of SEQ ID NO: 22 as SEQ ID NO: 91.

FIG. 8 discloses the RNA versions of SEQ ID NOS 80, 81, 83 and 84 as SEQ ID NOS 92-95, respectively, in order of appearance.

FIG. 9A) Total RNA from pEGFP-N1-3UTR-25nt transfected cells was isolated at indicated time points and qRT-PCR was performed for EGFP and GAPDH mRNAs with products visualized by ethidium bromide gel electrophoresis. FIG. 9B) Seventy-two hours after transfection total RNA was isolated from MVs and qRT-PCR was performed for EGFP and GAPDH mRNAs before and after DNaseI treatment. FIG. 9C) After MV collection, as in b, indicated DNAase and RNAse treatment were performed to MVs and/or their content. Similar qRT-PCR reactions were performed and the end product DNAs were loaded onto agarose gels. Representative gels shown.

FIG. 10 depicts the 3' UTR sequences of the plasmids that were used in the experiments described herein. Not-I and Afl-II restriction sites are shown in rectangles and the 25 nt zip code and mutants sequences are underlined once. Mutated bases are shown in italics. Partial SV40 sequence (bearing AAUAAA polyadenylation, shown bold, site) is double underlined.

FIG. 11 shows the alignment of the 3' UTR of mRNAs with potential miR-1289 binding sites. hsa-miR1289 (SEQ ID NO: 23); NM_003614.1 (SEQ ID NO: 24); NM_031309.4 (SEQ ID NO: 25); NM_001702.2 (SEQ ID NO: 26); NM_001080547.1 (SEQ ID NO: 27); NM_032192.2 (SEQ ID NO: 28); NM_001013635.2 (SEQ ID NO: 29); NM_152795.2 (SEQ ID NO: 30); NM_001001712.2 (SEQ ID NO: 31); NM_005764.3 (SEQ ID NO: 32); XM_928353.1 (SEQ ID NO: 33); NM_012272.1 (SEQ ID NO: 34); NM_199165.1 (SEQ ID NO: 35); NM_198576.2 (SEQ ID NO: 36); NM_181553.2 (SEQ ID NO: 37).

DETAILED DESCRIPTION

Figure 2:
FIG. 2 shows deep alignment of the 3'UTR of the top 20 enriched transcripts identified by the experiments described herein. The similarities between the 25 nt sequence and the 3'UTR sequences of top 20 transcripts were deciphered with BLAST pairwise alignment. Within the conserved regions, a 25 nt sequence was picked for further ClustalW alignment. The 5 nt core sequence "CTGCC" is shown in the red rectangles.

Aspects of the present invention relate to the discovery of a 25 nucleotide sequence in the 3' UTR of mRNAs, which serves to target the mRNA into microvesicles of a cell. Without being bound by theory, the nucleotide sequence is said to be "zip code-like" in its function in that it is recognized by cellular machinery that traffics molecules to various places within the cell. The incorporation of this sequence into the 3' UTR of a heterologous DNA (expressed coding sequence) and expression in a cell leads to enrichment of the expressed RNA in microvesicles of the cell. Critical features of this sequence are both a CUGCC core present on a stem loop structure and a miRNA binding site. Increasing the amount of the miRNA specific for the binding site further increases the enrichment of the mRNAs into microvesicles. This zip code functions in multiple cell types to target mRNA to microvesicles. As such, the identified zip code-like sequence can be incorporated into a specific RNA (e.g., by its presence in a DNA template) and used to target that RNA to microvesicles of the cell in which the RNA is transcribed.

One aspect of the present invention relates to a nucleic acid molecule comprising the nucleic acid sequence that promotes enrichment of an RNA into microvesicles/exosomes (referred to herein as a first nucleic acid sequence and/or the zip code sequence) operatively linked to a heterologous nucleic acid sequence that is expressed in a cell (referred to herein as the second nucleic acid sequence).

In the context of a DNA molecule, the appropriate linkage of the zip code sequence is sufficient to promote enrichment of a transcribed RNA into microvesicles, upon transcription of the appropriate DNA strand in a cell. In the context of an RNA molecule, the zip code sequence is sufficient to promote enrichment of the RNA into microvesicles produced by the cell in which it is present. Such linkage is referred to herein as operative, with respect to the promotion of enrichment of a transcribed RNA into microvesicles, and the first and second nucleic acid molecules are herein referred to as operatively linked, with respect to that function.

The suitable heterologous (second) nucleic acid sequence for linkage to the zip code sequence is one that is recognized for functional use by a cell. Such a DNA molecule will typically contain a coding sequence (e.g., an open reading frame suitable for translation into a protein) operatively linked to the appropriate regulatory sequences (TATA box, poly A site, etc) for transcription into an RNA by cellular transcription machinery. Such a RNA molecule (e.g., an mRNA) will likewise contain the appropriate sequences for function within the cell. That function will depend upon the nature of the RNA molecule. For example, an mRNA will contain sequences for recognition by cellular translation machinery, and will typically contain a polyA tail. The DNA molecule may contain a polyA site. A typical polyA site is AAUAAA. Multiple polyA sites can be present in the DNA molecule. One or more of the multiple sites may be preceded by the zip code sequence.

Nucleic Acids

A nucleic acid molecule, as used herein, can be RNA or DNA, and can be single or double stranded. Such nucleic acid molecules include, for example, but are not limited to, nucleic acid molecules encoding proteins. Other such nucleic acid molecules, for example, may act as transcriptional repressors, antisense molecules, ribozymes, small inhibitory nucleic acid sequences (e.g., RNAi, shRNAi, siRNA, stRNA, micro RNAi (mRNAi), antisense oligonucleotides etc.).

Various DNA molecules are envisioned for the nucleic acid molecule of this invention. Typically the DNA molecule will comprise regulatory sequences necessary and sufficient for transcription into an RNA molecule (e.g., one of the various forms discussed herein) by cellular machinery. In one embodiment, the DNA molecule encodes a protein and is first transcribed into an mRNA. The DNA that encoded the mRNA may contain splice sites, requiring that the mRNA be processed, or may alternatively lack splice sites (e.g., a cDNA). In another embodiment, the DNA molecule serves as a regulatory molecule. For example, the DNA molecule may encode for a siRNA.

Various forms of RNA molecules are envisioned for the nucleic acid molecule of this invention, including mRNA and ncRNA (non-coding RNA). mRNA (messenger RNA) is a molecule of RNA that encodes a chemical "blueprint" for a protein product. mRNA is transcribed from a DNA template, and carries coding information to the sites of protein synthesis: the ribosomes, where the nucleic acid polymer is translated into a polymer of amino acids. mRNA comprises contiguous sequence of nucleotides arranged into codons consisting of three bases each, with each codon encoding for a specific amino acid, the stretch of contiguous in-frame codons terminating with a stop codon, which terminate protein synthesis. mRNA also contain untranslated regions (5' and 3' UTR). An mRNA typically will contain a polyA at the 3' end. Many non-coding RNAs also contain a polyA site.

A non-coding RNA (ncRNA) is a functional RNA molecule that is not translated into a protein. Less-frequently used synonyms are non-protein-coding RNA (npcRNA), non-messenger RNA (nmRNA) and functional RNA (fRNA). The DNA sequence from which a non-coding RNA is transcribed is sometimes referred to as an RNA gene. Non-coding RNA include highly abundant and functionally important RNAs such as transfer RNA (tRNA) and ribosomal RNA (rRNA), as well as RNAs such as snoRNAs, microRNAs, siRNAs and piRNAs and the long non coding RNAs. Long non-coding RNAs (long ncRNAs, lncRNA) are non-protein coding transcripts longer than 200 nucleotides.

The term "short interfering RNA" (siRNA), also referred to herein as "small interfering RNA" is defined as an agent which functions to inhibit expression of a target gene, e.g., by RNAi. As used herein an "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow. shRNAs function as RNAi and/or siRNA species but differ in that shRNA species are double stranded hairpin-like structure for increased stability.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

The terms "microRNA" or "miRNA" are used interchangeably herein to refer to endogenous RNAs, some of which are known to regulate the expression of protein-coding genes at the posttranscriptional level. Endogenous microRNA are small RNAs naturally present in the genome which are capable of modulating the productive utilization of mRNA. Also included in the invention are artificial microRNAs. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule.

Any of these RNAs can be encoded by DNAs contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

In one embodiment the nucleic acid used in the invention is therapeutic when delivered to a subject in need thereof. In one embodiment, the therapeutic nucleic acid encodes an RNAi that results in the inhibition of gene expression in the subject. Delivery of the RNAi to the target cells by the method described herein serves to decrease expression of a target gene. For example, the RNAi can be designed to specifically inhibit a factor that is known to be overly abundant in a disease (such as amyloid-beta in Alzheimers disease) and the RNAi can be delivered to specific target cells known to express factor. In another embodiment, the therapeutic nucleic acid (DNA or RNA) encodes a protein, and can be used for gene therapy. In this way, targeted delivery of the microvesicles, or of the nucleic acid molecules, described herein, can promote the expression of the therapeutic nucleic acid in specific cells types or specific locations within a subject.

Zip Code Sequences

Figure 7:
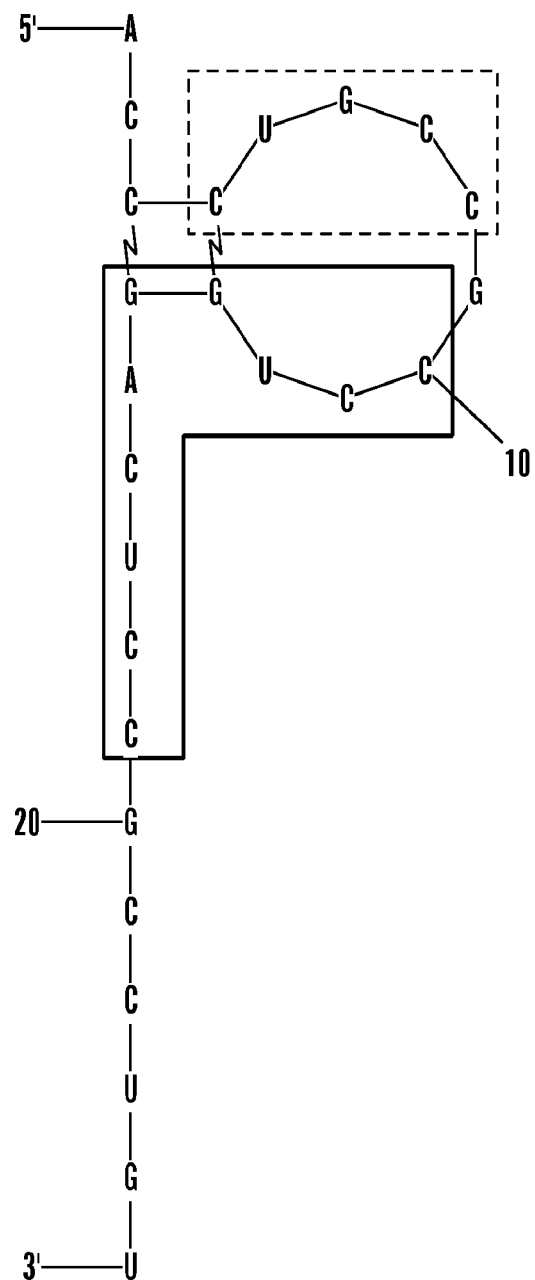
FIG. 7 depicts the secondary structure of the 25 nt zip code. A secondary structure for the full-length zip code sequence (SEQ ID NO: 22) was predicted by an RNA mFold program showing that these sequences can form a stem-loop secondary structure. Stem-loop bonds are shown as a "~". The core sequence "CTGCC" and miR-1289 binding site are shown within red and green rectangles, respectively.

The nucleotide sequence 5'-ACCCTGCCGCCTG-GACTCCGCCTGT-3' (SEQ ID NO: 22) and also 5'-AC-CCTGCCGCCTGGATCAAGCCTGT-3' (SEQ ID NO: 38) were each shown to confer enrichment of microvesicles localization to a RNA when present in the 3' untranslated region. In addition to these specific sequences, variants of these sequences are expected to similarly function to target an RNA to an microvesicles in a cell, as long as the core remains intact and the overall structure of the sequence adopts a stem loop structure similar to that shown in FIG. 7. Such variants are referred to herein as "functional variants". Whether a sequence adopts a stem loop structure can be predicted using a computer algorithm such as MFOLD (M. Zuker. Nucleic Acids Res. 31 (13), 3406-3415, 2003; Waugh, P. et al. RNA 8 (6), 707-717, 2002; M. Zuker & A. B. Jacobson, RNA 4, 669-679, 1998, as described herein. By way of example, the nucleotide sequences shown will tolerate nucleic acid substitutions at nucleotides that do not directly participate in the stem loop structure, that fall outside of the core sequences. Also, nucleic acid substitutions at nucleotides that participate in the stem loop structure can be tolerated as long as compensatory substitutions are made at the corresponding nucleotides to which they bind in the stem loop, such that the overall stem loop structure is preserved. For example, a G is substituted for a C, and the corresponding C to which is binds in the stem loop, is substituted for a G.

In one embodiment, the zip code-like nucleic acid sequence is 5'-ACCCTGCCGCCTGGACTCCGCCTGT-3' (SEQ ID NO: 22). In one embodiment, the zip code-like nucleic acid sequence is 5'-ACCCTGCCGCCTGGAT-CAAGCCTGT-3' (SEQ ID NO: 38). Other such nucleic acids described herein are also expected to function similarly, and as such are equally encompassed in the various embodiments of the invention described herein.

The disclosed zip code-like nucleic acid sequences are further expected to function as concatomers. As such, the invention encompasses a nucleic acid molecule described herein, wherein the first nucleic acid sequence comprises two or more contiguous copies of 5'-ACCCTGCCGCCTG-GACTCCGCCTGT-3' (SEQ ID NO: 22), or a functional variant thereof, 5'-ACCCTGCCGCCTGGATCAAGC-CTGT-3' (SEQ ID NO: 38), or a functional variant thereof, or combinations thereof, to thereby generate a concatomer. In one embodiment, the concatomer comprises two such contiguous sequences. In one embodiment, the concatomer comprises 3, 4, 5, 6, 7 or more such contiguous sequences. The sequences within the concatomer may be separated by one or more additional nucleotides. In one embodiment, the sequences are separated by 1, 2, 3, 4, 5, 6, 7, 8, 9, 10 or more additional nucleotides. In one embodiment, the sequences are separated by 11, 12, 13, 14, 15, or more additional nucleotides.

The zip code sequence is expected to function when present at a variety of locations in the nucleic acid molecule. In one embodiment, zip code-like (first) nucleic acid sequence is located 3' to the heterologous nucleic acid sequence (second). The zip code sequence can be located directly adjacent the heterologous nucleic acid sequence, or can be separated by intervening sequence (e.g., 1-5 nt, 6-10 nt, 20, 30, 40, 50, 60, 70, 80, 90, 100 nt or more). In one embodiment, the second heterologous sequences encodes an mRNA and the zip code sequence is located downstream of a translation stop site of the mRNA.

In one embodiment, the zip code nucleic acid sequence is located 5' of a poly A site (DNA) or polyA tail (RNA). The zip code sequence can be located directly adjacent a poly A site/polyA tail, or can be separated by intervening sequence. The intervening sequence can be short (e.g., within 1, 2, 3, 4, 5, 6, 7, 8, 9 or 10 bases), although longer intervening sequences are also envisioned (e.g., greater than 10 bases, such as 15, 20, 25, 30, 35, 40 bases, etc.).

Expression Vectors

The nucleic acid molecules of the invention can be present in the context of an expression vector and/or a cloning vector. Such vectors are typically specifically designed for the host cell in which they are to be used (e.g., prokaryotic, eukaryotic or both).

Expression vector may be, for example, plasmid or virus vectors, and typically contain an origin of replication, a promoter and a regulator of the promoter. The recombinant expression vector may then be used to transform or transfect suitable host cells such as bacterial cells, e.g. *E. coli* cells, or eukaryotic cells such as yeast, insect or preferably, mammalian cells, to provide for expression of a nucleic acid sequence described herein. Suitable bacterial and eukaryotic expression vectors are commercially available and well known in the art and their use is described, e.g., in Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994).

Many mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of nucleic acids in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

Many such vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. Many viral vectors or virus-associated vectors are known in the art. Such vectors can be used as carriers of a nucleic acid construct into the cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cells genome. The constructs may include viral sequences for transfection, if desired. Alternatively, the construct may be incorporated into vectors capable of episomal replication, e.g. EPV and EBV vectors.

Expression and cloning vectors usually contain one or more regulatory sequences (e.g., a promoter) operably linked to the encoding nucleic acid sequence to direct RNA synthesis. Promoters recognized by a variety of potential host cells are well known. Promoters suitable for use with prokaryotic hosts include the beta-lactamase and lactose promoter systems (Chang et al., Nature, 275:615 (1978); Goeddel et al., Nature, 281:544 (1979)), alkaline phosphatase, a tryptophan (trp) promoter system (Goeddel, Nucleic Acids Res., 8:4057 (1980); EP 36,776), and hybrid promoters such as the tac promoter (deBoer et al., Proc. Natl. Acad. Sci. USA, 80:21-25 (1983)). Promoters for use in bacterial systems also will contain a Shine-Dalgarno (S.D.) sequence operably linked to the encoding DNA. Promoters for vectors in mammalian host cells can be obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems. The promoter sequence may be a "tissue-specific promoter," which means a nucleic acid sequence that serves as a promoter, i.e., regulates expression of a selected nucleic acid sequence operably linked to the promoter, and which affects expression of the selected nucleic acid sequence in specific cells.

Transcription of a DNA by higher eukaryotes may be increased by inserting an enhancer sequence into the vector. Enhancers are cis-acting elements of DNA, usually about from 10 to 300 bp that act on a promoter to increase its transcription. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be present at a position 5' or 3' to the coding sequence, but is preferably located at a site 5' from the promoter.

Expression vectors used in eukaryotic host cells (yeast, fungi, insect, plant, animal, human, or nucleated cells from other multicellular organisms) may also contain sequences necessary for the termination of transcription and for stabilizing the RNA. Such sequences are commonly present at the 5' and, occasionally 3', untranslated regions of eukaryotic or viral DNAs or cDNAs. These regions contain nucleotide segments transcribed as polyadenylated fragments in the untranslated portion of the RNA.

Cells

Another aspect of the invention relates to a cell, or population thereof, comprising a nucleic acid molecule comprising a first zip code nucleic acid sequence (e.g., 5'-ACCCTGCCGCCTGGACTCCGCCTGT-3' (SEQ ID NO: 22), or a functional variant thereof), operably linked to a second, heterologous nucleic acid sequence. The cell may be in vitro (e.g., a cell in culture) or in vivo. The cell may be eukaryotic or prokaryotic. Prokaryotic cells are useful for the manipulation and large scale production of nucleic acid sequences. Such cells include bacterial cells and yeast cells. Examples of eukaryotic cells are mammalian cells, insect cells, invertebrate cells, and avian cells. Mammalian cells typically used in the laboratory include mouse, rat, human, non-human primate cells. A variety of different cells types are envisioned for use in the invention. In one embodiment, the cells are mammalian, and comprise the nucleic acid molecule described herein in expressible form. In one embodiment, the cells express the nucleic acid molecule, described herein. In one embodiment, the cells result from transient transfection of an expression vector comprising the nucleic acid molecule. In one embodiment, the cells result from stable transfection of the nucleic acid molecule described herein via an expression vector. In one embodiment, the cells further comprise a pre-miR-1289, in expressible form. In one embodiment, the cells further express miR-1289.

Cells capable of producing microvesicles can be used to generate microvesicles that are enriched for RNAs comprising the zip code-like sequence described herein. Microvesicles are secreted naturally by various types of cells, in particular by epithelial cells, tumor cells and certain cells of the immune system, (mast cells, T and B lymphocytes, dendritic cells, especially Langerhans cells). In one embodiment, the cell is a eukaryotic cell comprising internal vesicles for secretion, which can be cultivated, which is capable of exocytosis, which is genetically modifiable. In one embodiment, the cell secretes the internal vesicles when exposed to an external stimulus. Cells that can produce microvesicles include, without limitation, skin fibroblasts, mast cells, T and B lymphocytes and dendritic cells (for example Langerhans cells), or cells derived from these cell types, and cells or cell lines modified by genetic engineering so as to render them capable of secreting microvesicles.

In one embodiment, the cell is a continuous cell line or a tumor-derived cell line (e.g., originating from the subject to whom the generated microvesicles will be administered).

In one embodiment, the cell type is useful to generate microvesicles in vitro. In one embodiment the cell is a primary cell, obtained from a multicellular organism and grown or propagated in the laboratory for a short period of time (e.g., 10 or fewer passages, 50 or fewer passages, 100 or fewer passages). Such a primary cell may be a cell obtained from a subject, to which microvesicles produced therefrom, or the cells engineered to produce enriched microvesicles, will be administered. In one embodiment, the cells are immature dendritic cells (e.g., generated from harvested bone marrow). In one embodiment, the immature dendritic cells are devoid of T-cell activators (e.g., MHC-II AND/OR CD86). Methods of producing microvesicles from immature dendritic cells are known in the art and can be adapted for use with the instant invention (US Published Patent Application 2004/0241176).

Exosomes/Microvesicles

Other aspects of the invention relate to the production of microvesicles that are enriched for a specific RNA sequence. Such a specific RNA sequence is herein referred to as a target RNA sequence. Microvesicles enriched for the presence of the target RNA sequence are produced from cells that contain a target nucleic acid sequence in the context of the nucleic acid molecule of the present invention. One aspect of the invention is an in vitro method of producing a microvesicle or preparation thereof, comprising a target RNA sequence. The method involves generating a DNA molecule comprising a zip code sequence operatively linked to a heterologous DNA sequence that encodes the target RNA sequence (second sequence), in expressible form. Cells in culture are then transfected with an effective amount of the DNA molecule under conditions suitable for expression. Cells expressing the DNA molecule are subjected to conditions suitable for production of microvesicles. Microvesicles generated by the cells are isolated from the culture, to thereby produce a preparation of microvesicles enriched for the specific RNA sequence. The cells used are preferably cells known to produce microvesicles. Such cells are known in the art. Conditions suitable for expression of the DNA molecule include, without limitation, conditions whereby the cells are dividing in culture. These conditions assume a minimum amount of time necessary for the uptake and expression of the DNA molecule by the transfected cells (typically 1-2 days).

The method may further involve increasing the miR-1289 in the recipient cells. This can be accomplished, for example, by transfecting the cells with an effective amount of a pre-miR-1289 in expressible form, under conditions suitable for expression. In one embodiment, the DNA molecule and the pre-miR-1289 are each transfected in the context of expression vectors (e.g., separate vectors or on the same vector molecule, such as in an expression cassette). miR expression vectors are known in the art and commercially available. The cells can alternatively be engineered to constitutively express increased miR-1289 (e.g., via stable incorporation and expression of a pre-miR-1289). Another aspect of the invention relates to such cells engineered to have increased miR-1289.

In one embodiment, microvesicles, or a preparation thereof, produced by the method described herein contain at least a comparable amount of the target RNA as any other given RNA therein. Increased amount of the target RNA as compared to any other given RNA therein may also be obtained. In one embodiment, the target RNA is present in an amount that is at least about 10%, 20%, 30% 40%, 50%, 60%, 70% 80% or 90%, more than another given RNA therein. Higher levels of enrichment may also be achieved. In one embodiment, the target RNA is present in the microvesicle or preparation thereof, when compared to other RNAs within the microvesicles, by at least 2 fold. Higher fold enrichment may also be obtained (e.g., 3, 4, 5, 6, 7, 8, 9 or 10 fold). In one embodiment, the target RNA is present in at least about 10%, 20%, 30%, 40%, 50%, 60%, 70%, 80%, or 90% of the microvesicles of the obtained preparation.

One aspect of the invention relates to a microvesicle that contains one or more target RNA molecules in the context of a nucleic acid molecule described herein. Such a microvesicle is produced by the herein described methods. Another aspect of the invention relates to a microvesicle preparation that comprises one or more such microvesicles, generated by the herein described methods. As the term is used herein, a microvesicle preparation refers to a population of microvesicles obtained/prepared from the same cellular source. Such a preparation is generated, for example, in vitro, by culturing cells expressing the nucleic acid molecule of the instant invention and isolating microvesicles produced by the cells. Methods of isolating such microvesicles are known in the art (Thery et al., Isolation and characterization of exosomes from cell culture supernatants and biological fluids, in *Current Protocols Cell Biology*, Chapter 3, 322, (John Wiley, 2006)), examples of which are described herein. Typically the microvesicles in a preparation will be a heterogeneous population, but the RNAs contained within the preparation will comprise the target RNA sequence.

In one embodiment, the microvesicles, or preparation thereof, further comprises a targeting ligand. Such a targeting ligand may be used to direct the microvesicles to specific cells with which they will ultimately fuse. Such a targeting ligand can be produced, for example, by engineering the cells used to produce the microvesicles to express a protein abundantly present in exosomal membranes (e.g., Lamp2b) as a fusion protein with the targeting ligand. The targeting ligand is typically a member of a specific binding pair, the other of which is found on the target cells (Alvaret-Erviti et al., Nature Biotechnology 29: 341-345 (2011)). In one embodiment, the targeting ligand is an antibody or antigen binding fragment thereof (e.g., a single chain antibody (scFV)) that specifically binds a marker present on cellular target.

Delivery of Therapeutic Nucleic Acid Molecules

Aspects of the present invention relate to methods for delivering a therapeutic nucleic acid (e.g., RNA) to a subject. Nucleic acid sequences that are therapeutic to a subject can be engineered for targeting into microvesicles using the methods described herein. Such nucleic acid sequences can then be delivered to the subject in one or more forms. In one embodiment, microvesicles are generated in vitro that contain the therapeutic nucleic acid. An effective amount of these "engineered" microvesicles is then administered to the subject (e.g., by intravenous administration, or direct injection into a tissue or organ). In one embodiment, the microvesicles further comprise an effective amount of pre-miR-1289 in expressible form, or an miRNA 1289 resulting from processing of the pre-miR-1289, or a combination thereof.

In another embodiment, an effective amount of a nucleic acid molecule comprising the therapeutic nucleic acid, operatively linked to the zip code sequence, in expressible form, is administered directly to the subject. In one embodiment, a pre-miR-1289 in expressible form is also administered (e.g., present in the same expression vector as the nucleic acid molecule). In one embodiment, the nucleic acid molecule is a DNA molecule. The exogenous DNA molecule is administered by methods that promote uptake of the nucleic acid by cells of the subject known to secrete microvesicles. One such method is microinjection into cells of the subject. The DNA molecule is in a form that is expressible by the cells once taken up. As such, the RNA molecule transcribed from the exogenous DNA molecule is enriched in microvesicles produced by the cells. This promotes a "bystander effect" to increase the distribution of the nucleic acid into cells in the region of administration. Such a method is particularly suitable for delivery of target nucleic acid to regions such as the brain.

Pharmaceutical Compositions

In one embodiment, the nucleic acid molecule or microvesicle preparation described herein is an active ingredient in a composition comprising a pharmaceutically acceptable carrier. Such a composition is referred to herein as a pharmaceutical composition. A "pharmaceutically acceptable carrier" means any pharmaceutically acceptable means to mix and/or deliver the targeted delivery composition to a subject. The term "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the composition and is compatible with administration to a subject, for example a human. Such compositions can be specifically formulated for administration via one or more of a number of routes, such as the routes of administration described herein. Supplementary active ingredients also can be incorporated into the compositions. When an agent, formulation or pharmaceutical composition described herein, is administered to a subject, preferably, a therapeutically effective amount is administered. As used herein, the term "therapeutically effective amount" refers to an amount that results in an improvement or remediation of the condition.

Administration

Administration of the pharmaceutical composition is by means which the nucleic acid molecule or microvesicle contained therein will contact the target cell. Examples of such routes are localized and systemic, which include, without limitation parenteral, enteral, and topical administration. Parenteral administration is usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. Administration can be systemic administration, or localized, as determined necessary by the skilled practitioner. Localized administration can be directed to the location of the target cells or target tissue (e.g., brain cells or tumor cells). In one embodiment administration is intratumoral (e.g., by injection into a tumor). In the case of the nucleic acid molecule, the administration can be directly into the target cell (e.g., by microinjection).

Pharmaceutical compositions and formulations for specified modes of administration, described herein are also encompassed by the present invention.

Inhibition of Microvesicle Incorporation of RNA

Another aspect of the invention relates to a method of inhibiting RNA incorporation into microvesicles by a cell. The method comprise inhibiting the endogenous miR-1289 in the cell. Methods of inhibiting miRs in a cell are known in the art. In one embodiment, the endogenous miR-1289 is inhibited by transfection of the cell with an effective amount of an anti-miR-1289 sequence. Such anti-miR's are commercially available.

The cell can be in vitro or in vivo. The in vitro cell can be a cell in culture. The in vivo cell can be a cell within a subject (e.g., a tumor cell). In one embodiment, the cell is a tumor cell in a subject. Inhibition of RNA incorporation into microvesicles in a tumor cell in a subject is accomplished, for example, by administration of an anti-miR-1289 to the subject, to thereby contact the tumor cells (e.g., by intratumoral injection).

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs.

1. An isolated nucleic acid molecule comprising a first nucleic acid sequence 5'-ACCCTGCCGCCTGGACTC-CGCCTGT-3' (SEQ ID NO: 22), or a functional variant thereof, operably linked to a second, heterologous nucleic acid sequence.
2. The isolated nucleic acid molecule of paragraph 1 selected from the group consisting of DNA and RNA.
3. The isolated nucleic acid molecule of paragraph 2, wherein the nucleic acid molecule is DNA and wherein the DNA is in the context of an expression vector.
4. The isolated nucleic acid molecule of paragraph 2, wherein the nucleic acid molecule is RNA and the RNA is selected from the group consisting of mRNA, shRNA, and ncRNA.
5. The isolated nucleic acid molecule of paragraph 1, wherein the first nucleic acid sequence is located 3' of the second nucleic acid sequence.
6. The isolated nucleic acid molecule of paragraph 5, wherein the nucleic acid molecule is DNA and the first nucleic acid sequence is located 5' of a poly adenylation site (DNA).
7. The isolated nucleic acid molecule of paragraph 5, wherein the nucleic acid molecule is RNA and the first nucleic acid sequence is located 5' of a poly adenylation sequence.
8. A microvesicle comprising a RNA molecule comprising a first nucleic acid sequence 5'-ACCCTGCCGCCTG-GACTCCGCCTGT-3' (SEQ ID NO: 22), or a functional variant thereof, operably linked to a second heterologous nucleic acid sequence.
9. The microvesicle of paragraph 8, wherein the RNA molecule is selected from the group consisting of mRNA, shRNA, and ncRNA.
10. The microvesicle preparation of any one of paragraphs 8 or 9, wherein the first nucleic acid sequence is located 3' of the second nucleic acid sequence.
11. The microvesicle of any one of paragraphs 8-10, wherein the first nucleic acid sequence is located 5' of a poly A sequence.
12. An in vitro microvesicle preparation comprising a microvesicle of any of paragraphs 8-11.
13. An in vitro method of producing a microvesicle preparation enriched for a specific RNA sequence, comprising:
a) transfecting cells in vitro with a DNA molecule in expressible form, comprising a first nucleic acid sequence 5'-ACCCTGCCGCCTGGACTCCGCCTGT-3' (SEQ ID NO: 22), or a functional variant thereof, operably linked to a second, heterologous nucleic acid sequence, under conditions suitable for expression; and
b) isolating microvesicles generated by the transfected cells of step a);
to thereby produce a microvesicle preparation enriched for the specific RNA sequence.
14. The method of paragraph 13, further comprising transfecting the cells with a pre-miR-1289 in expressible form under conditions suitable for expression.
15. The method of any one of paragraphs 13 or 14, wherein the specific RNA sequence is selected from the group consisting of a mRNA, a shRNA, and a regulatory ncRNA.
16. The method of any one of paragraphs 13-15, wherein transfection is by lipofection.
17. The method of any one of paragraphs 13-16, wherein the cells are primary cells or a continuous cell line.
18. The method of paragraph 17, wherein the cells are dendritic cells.
19. A method of delivering a therapeutic RNA to a subject, comprising, administering to the subject a microvesicle preparation enriched for the therapeutic RNA sequence, generated by the method of any one of paragraphs 13-18.
20. The method of paragraph 19, wherein administering is by systemic injection or local delivery to a site of target tissue.
21. The method of paragraph 20, wherein administering is by injection into a tumor.
22. The method of any one of paragraphs 19-21, wherein the therapeutic RNA is selected from the group consisting of a pre-miR, a non-coding regulatory RNA, a coding mRNA, and combinations thereof.
23. A method of delivering a therapeutic molecule to a subject, comprising: delivering to a cell of the subject a DNA molecule in expressible form, comprising a first nucleic acid sequence 5'-ACCCTGCCGCCTGGACTC-CGCCTGT-3' (SEQ ID NO: 22), or a functional variant thereof, operably linked to a second, heterologous nucleic acid sequence, under conditions suitable for expression.

24. The method of paragraph 23, wherein the DNA molecule further comprises a pre-miR-1289 in expressible form.

25. The method of any one of paragraphs 23 or 24, wherein the DNA molecule is in the context of a viral expression vector.

26. A method of inhibiting incorporation of RNA into microvesicles by a cell comprising, inhibiting endogenous miR-1289 in the cell, to thereby inhibit RNA incorporation into microvesicles by the cell.

27. The method of paragraph 26, wherein inhibiting endogenous miR-1289 is by transfection with an anti-miR-1289 sequence.

The invention is further illustrated by the following examples, which should not be construed as further limiting.

EXAMPLES

Example 1

In this study, the existence of a sequence in the 3' UTR of a subset of mRNAs that are enriched in MVs hypothesized to serve as a zip code to target them into MVs was investigated. Multiple sequence alignment analysis comparing the cellular transcriptome of human primary glioblastoma multiforme (GBM) cells with the transcriptome of MVs derived from them [5], revealed a stem loop forming sequence of 25 nt, variations of which were present in some of the most MV-enriched mRNAs. This putative zip code sequence contained a single miRNA binding site for miR-1289, as well as a CTGCC core sequence. Mutational analysis showed that these sequences cooperated in enrichment of a reporter mRNA in MVs and that upregulation of miR-1289 levels in cells further enhanced MV enrichment.

Results

Figure 1:
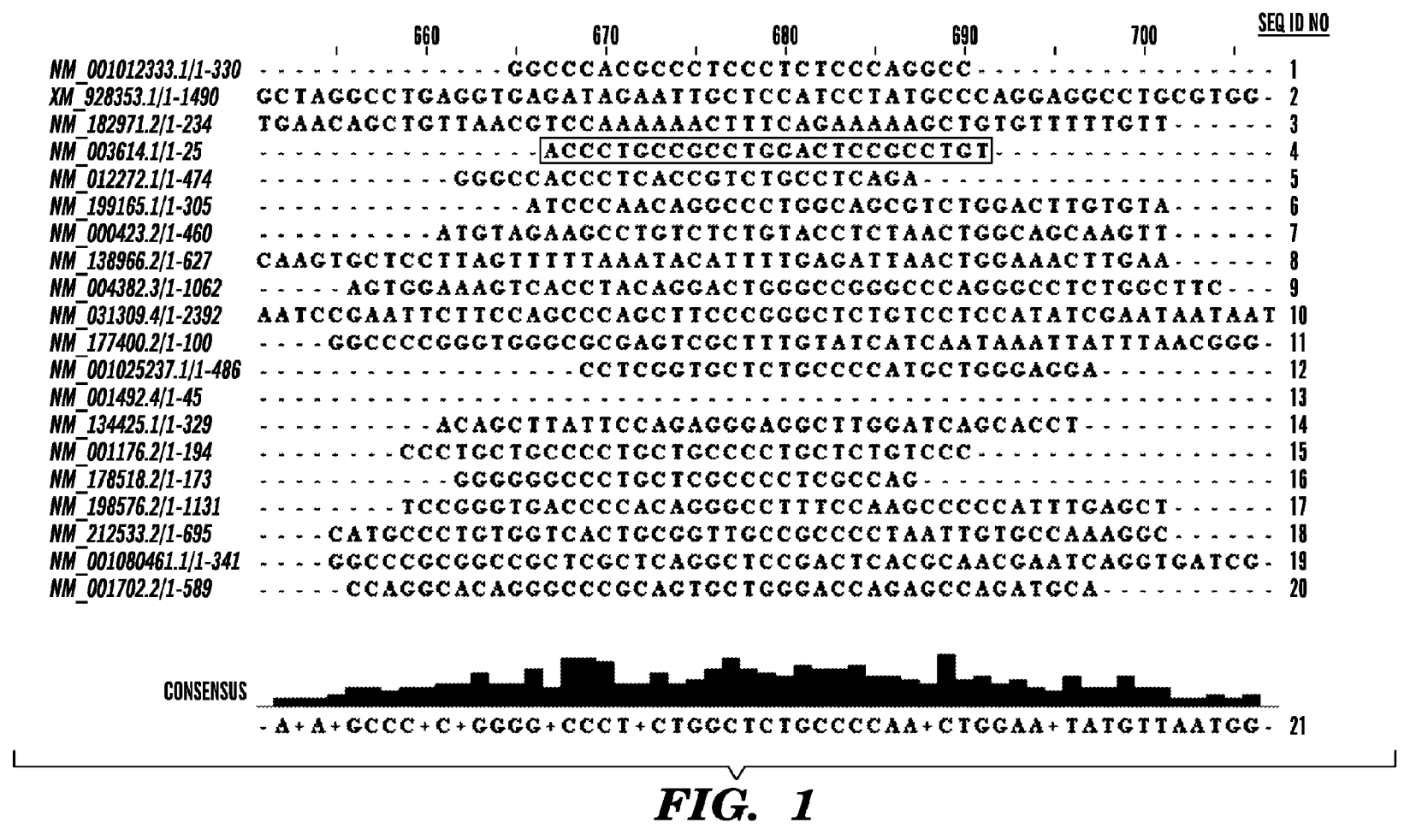

Microarrays of the mRNAs Isolated from GBM-Derived MV Reveals a Zip Code Like Sequence To test the hypothesis that there is a sequence in the 3' UTR of mRNAs that are enriched in MVs which serves as a zip code to target them to MVs, analysis was performed on microarray studies of the RNA content of two human primary GBM cells and two primary melanomas, and MVs derived from them. Focus was put on the 20 mRNAs most enriched in MVs as compared to cells of origin (Table 1), with extensive analysis of 3'UTR sequences of these mRNAs using a multiple alignment program (Clustal W2). Among those 20 transcripts, NM_003614.1 (mRNA GalR3) gave the highest pairwise alignment score within the list. Hence, evaluation was performed on the 25 nt sequence of this transcript with the highest consensus among these enriched mRNAs (FIG. 1). The similarities between this 25 nt sequence and the 3'UTR sequences of the top 20 MV-enriched transcripts was later deciphered with BLAST pairwise alignment. Within the conserved regions, 25 nt were picked for further ClustalW alignment which resulted in a 5 nt core sequence "CTGCC" (or variations CTGC, CTCCC, CGCCC, TGCC) shown in a rectangle in 11 of these 20 MV-enriched mRNAs (FIG. 2).

TABLE 1

The list of top 20 RNAs enriched in MVs

| Gene Symbol | Source_Reference_ID | Enrichment ratio MVs:cells |
|---|---|---|
| MDK | NM_001012333.1 | 49.86 |
| LOC653602 | XM_928353.1 | 45.93 |
| COX8C | NM_182971.2 | 42.79 |
| GALR3 | NM_003614.1 | 38.26 |
| PRPF40B | NM_012272.1 | 34.64 |
| ADSSL1 | NM_199165.1 | 33.67 |
| KRT2 | NM_000423.2 | 32.28 |
| NETO1 | NM_138966.2 | 31.69 |
| CRHR1 | NM_004382.3 | 31.34 |
| SCRT1 | NM_031309.4 | 30.66 |
| NKX6-2 | NM_177400.2 | 29.89 |
| TSPAN4 | NM_001025237.1 | 28.26 |
| GDF1 | NM_001492.4 | 27.81 |
| SLC26A1 | NM_134425.1 | 27.29 |
| ARHGDIG | NM_001176.2 | 26.84 |
| TMEM102 | NM_178518.2 | 26.28 |
| AGRN | NM_198576.2 | 25.96 |
| ABCA2 | NM_212533.2 | 24.82 |
| UNCX | NM_001080461.1 | 24.81 |
| BAI1 | NM_001702.2 | 24.66 |

Zip Code Fused to the EGFP mRNA is Functional

Figure 3A:
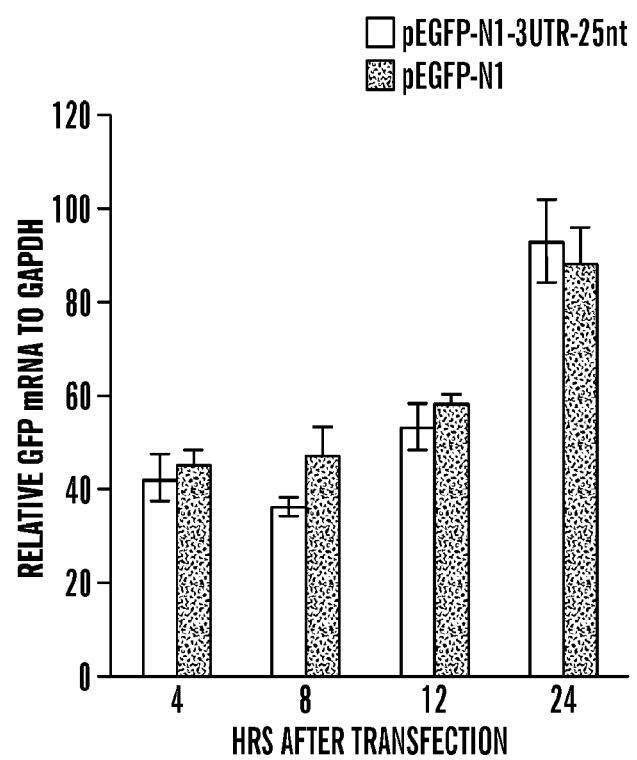

To examine the possible effect of this 25 nt sequence on incorporation of mRNA molecules into MVs, this sequence was incorporated into the pEGFP-N1 plasmid (Clontech, Mountainview, Calif.) by removing most of the original 3' UTR sequence of the EGFP mRNA. The resulting plasmid expressed EGFP mRNA fused to this potential zip code, followed by a polyA addition site and referred to here as pEGFP-N1-3UTR-25nt. Intact pEGFP-N1 plasmid was used as a control. It was first determined whether the new EGFP mRNA was stable without its original 3'UTR. HEK-293T cells were transfected with either wild-type EGFP expressing plasmid pEGFP-N1 or pEGFP-N1-3UTR-25nt. Twenty-four hours later, total RNA was isolated from cells and qRT-PCR was performed for EGFP mRNA. As shown in FIG. 3A, a similar increased accumulation of the EGFP mRNA 24 hours after transfection was observed with both pEGFP-N1 and pEGFP-N1-3UTR-25nt constructs. To evaluate whether the EGFP mRNA fused to the "25 nt sequence" was efficiently translated into EGFP protein, these transfected cells were also examined by fluorescence microscopy. As shown in FIGS. 3B and C, similar EGFP protein expression levels were observed for pEGFP-N1 (lane 1 and 2) and pEGFP-N1-3UTR-25nt (lane 3 and 4) over time suggesting that 25 nt long sequence is compatible with stability and efficient translation.

Figure 8:
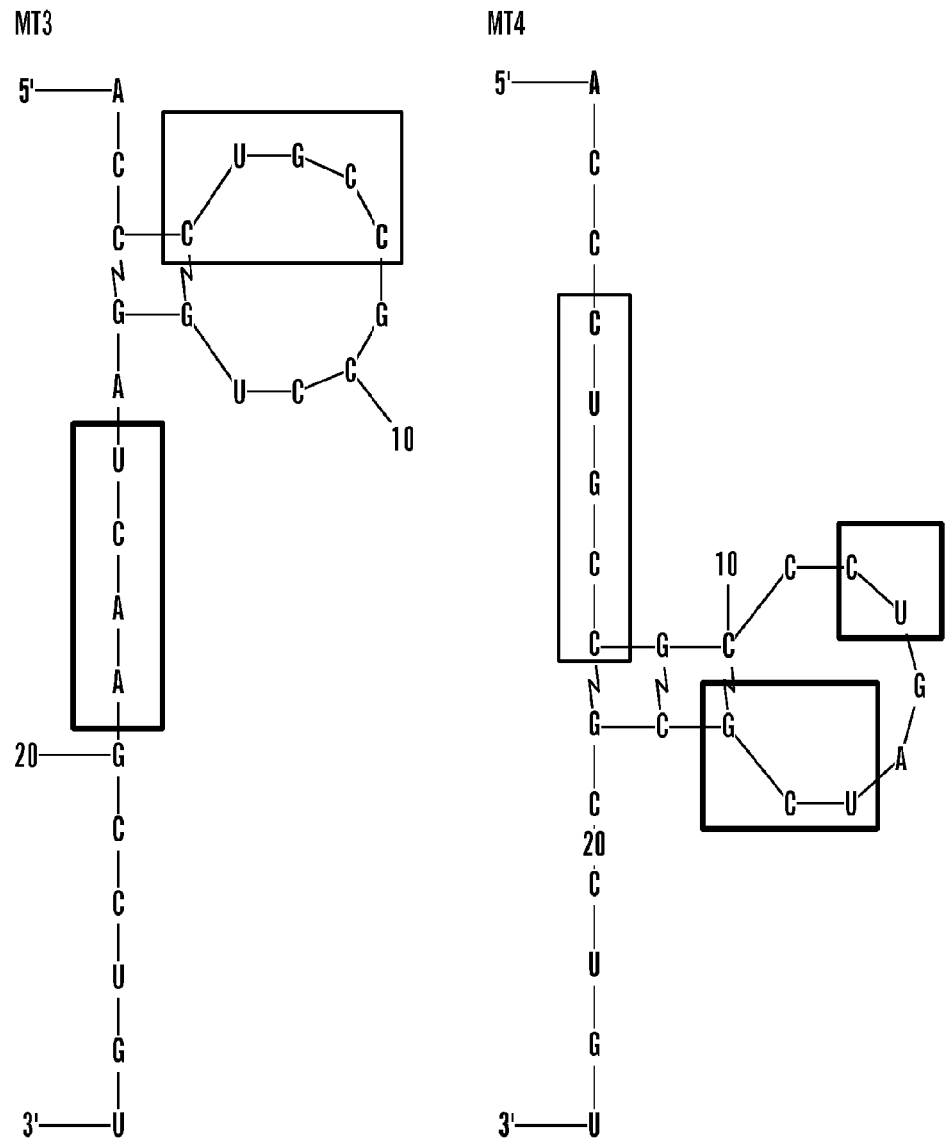
FIG. 8 depicts the secondary structure of the zip code mutated sequences. Secondary structure and stem-loops for zip code mutated sequences MTI (SEQ ID NO: 80), MT2 (SEQ ID NO: 81), MT3 (SEQ ID NO: 83) and MT3 (SEQ ID No: 84) were predicted using the RNA mFold program. Stem-loop bonds are shown as a "~". The core sequence "CTGCC" and miR-1289 binding site are shown within normal-lined and dashed-lined rectangles, respectively. Bolder rectangles highlight the mutations introduced to each sequence.
Figure 9A:
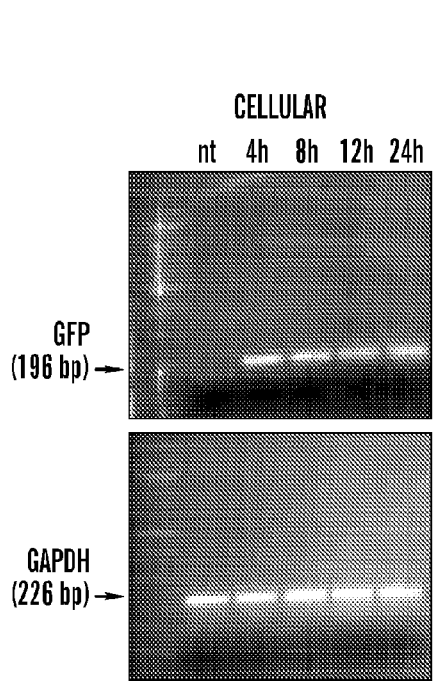
FIG. 9A-FIG. 9C shows data in the form of photographs of gel fractionated nucleic acids. The results indicate that EGFP mRNAs bearing zip code 3'UTR are stable and able to be transported into MVs. HEK-293T cells were non-transfected (nt) or transfected with pEFGP-N1 or pEGFP-N1-3UTR-25nt plasmids.
Figure 9B:
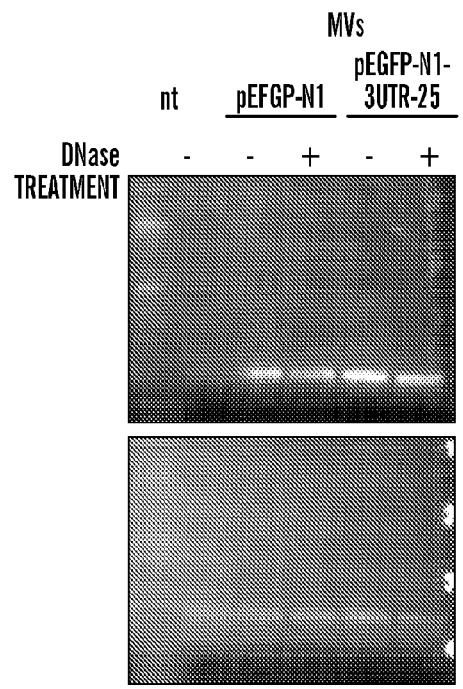
Figure 9C:
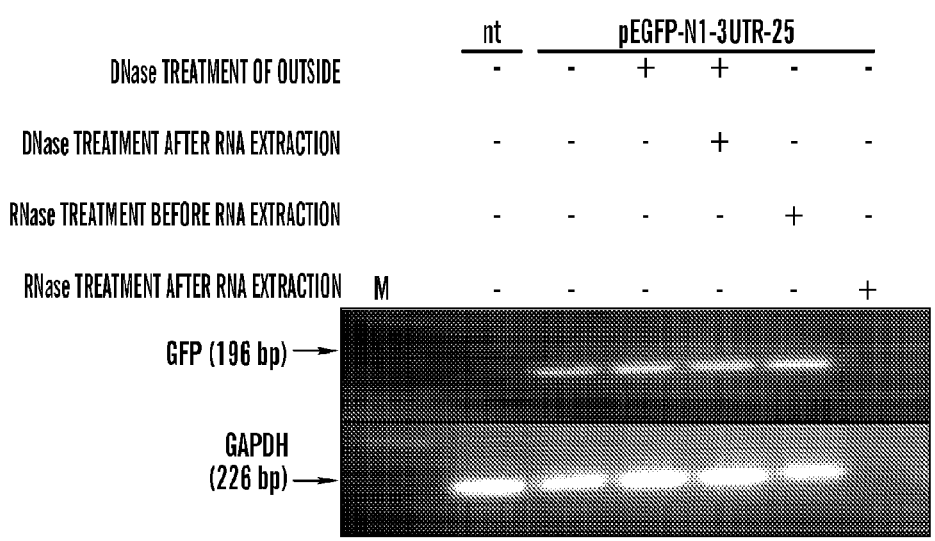

Next, experiments were performed to test whether this 25 nt sequence might be sufficient for enrichment of EGFP mRNA's in MVs. HEK-293T cells were transfected either with control plasmid or pEGFP-N1-3UTR-25nt and 72 hours later, MVs and cells were harvested, followed by performance of qRT-PCR for EGFP and GAPDH mRNAs. An increased amount of EGFP mRNA sequence was observed in MVs by about 2-fold, as compared with the original construct (FIG. 4A). Whether the presence of the 5 nt core sequence "CTGCC" is required for enrichment was also tested. When the 5 nt core sequence was mutated in two different ways, namely MT1 and MT2, (FIG. 4B, FIGS. 7 and 8), mRNA enrichment inside the MVs was inhibited (FIG. 4C). To avoid any plasmid DNA contamination during MV isolation, samples were treated with DNase before q-RT-PCR reaction, confirming that the data observed is due to mRNA content in MVs (FIGS. 9A and B). Moreover, to investigate the origin of the signal received by qPCR, the following treatments were performed: DNaseI on the outside of MVs and content of MVs, and RNase treatment before and after RNA isolation from MVs. As shown in FIG. 9C, DNaseI treatment did not prevent amplification of the PCR product, whereas after RNase treatment of the contents of MVs, no signal was observed suggesting that the signal observed in the experimental conditions came from mRNAs isolated from inside of the MVs not from any plasmid DNA contamination during MVs isolation or mRNAs attachment to the MVs.

miR-1289 Directly Binds to 25 Nt Zip Code and, in Part, has a Cooperative Role in the Enrichment of mRNAs within MVs The role of the miRNA binding sequence in the 3' UTR region of the reporter mRNA in transfer of the EGFP-25 nt mRNA into MVs was further investigated. Based on the facts that miRNAs are a family of 19 to 24 nt non-coding RNAs that inhibit the expression of target mRNAs by binding to complementary sequences in the UTRs of mRNAs (typically the 3' UTR) and repressing translation and/or cleaving the mRNA, it was hypothesized that an miRNA might be involved in this MV targeting mechanism. To test this hypothesis, a miRNA database search was performed within the 25 nt putative zip code sequence, and a potential binding site for miR-1289 was found (FIG. 5a). Strikingly, when cells were co-transfected with the EGFP-25nt cassette and pre-miR-1289, MV enrichment of the mRNA increased to 6-fold, whereas when endogenous miR-1289 was silenced by transfection with its antimiR-1289 sequence, inhibition of EGFP-25 nt mRNA enrichment within MVs was observed (FIG. 5B). In these experimental conditions, after transfection of pre-miR-1289, miR-1289 levels were increased approximately 100-fold in cells and 40-fold in MVs as assessed by qRT-PCR, while endogenous miR-1289 levels in cells were below the detection level of RT-PCR after inhibition of miR-1289 by anti-miR-1289. The miR-1289-mediated enrichment process was not due to the excessive expression of it either in HEK-293T or primary GBM cells, because miR-1289 was found to be expressed in low levels in those cells. The role of the potential miR-1289 binding sequence in MV targeting of the mRNA was further tested by generating point mutations within the miR-1289 target sequence (FIG. 8; MT3 and MT4) and it was observed that a mutation in the miR-1289 binding site (MT4) led to significant reduction in the accumulation of the EGFP-25nt mRNAs in MVs (FIG. 5C). The finding that the MT3 mutation did not dramatically inhibit the accumulation of the EGFP mRNA in MVs suggests that not only the miR-1289 binding site, but also the intact core sequence within the stem loop structure are involved in miR-1289-meditated transfer of mRNAs into MVs.

Figure 5D:
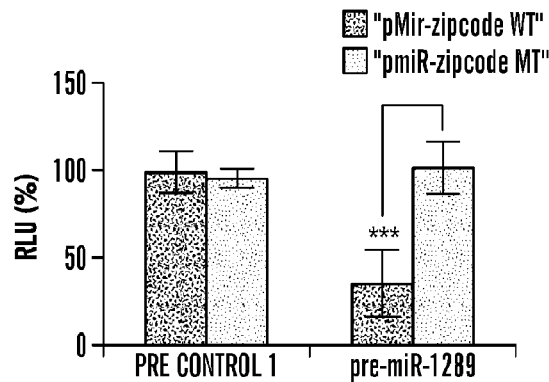
Figure 5E:
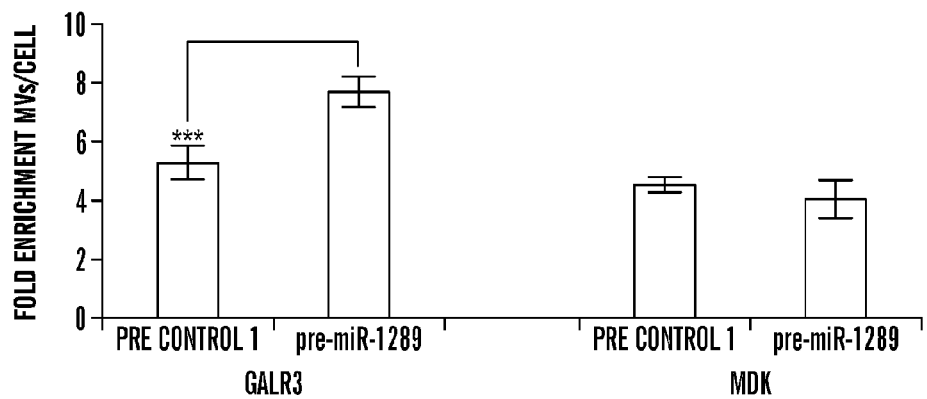

To test whether miR-1289 directly binds to this 25 nt sequence, constructed pMir-Reporter plasmids carrying either the wild-type 25 nt zip code or a zip code with mutations in the core binding site of miR-1289 were constructed. The same mutations were introduced into pMir-Reporter vectors as in MT4 (FIG. 8). Co-transfection of the wild-type pmiR-zip code and pre-miR-1289 resulted in significantly decreased luciferase activity as compared with transfection with pre-control 1, while transfection with the MT4 mutated sequence did not affect activity levels (FIG. 5D). In order to test whether miR-1289 overexpression could affect MV incorporation of endogenous mRNAs, two mRNAs were chosen from Table 1 based on their miR-1289 binding status, and similar experiments as performed for FIG. 5B were performed for GALR3 (one miR-1289 binding site in the 3'UTR) and MDK (no miR-1289 binding site) mRNAs. It was found that miR-1289 expression significantly increased GALR3 mRNA ratio (MVs/cell) by approximately 50%, as compared to pre control 1, whereas miR-1289 had no effect on the level of MDK mRNA in MVs (FIG. 5E). These data indicate that miR-1289-mediated enrichment via the zip code sequence functions for endogenous mRNAs as well.

Figure 6A:
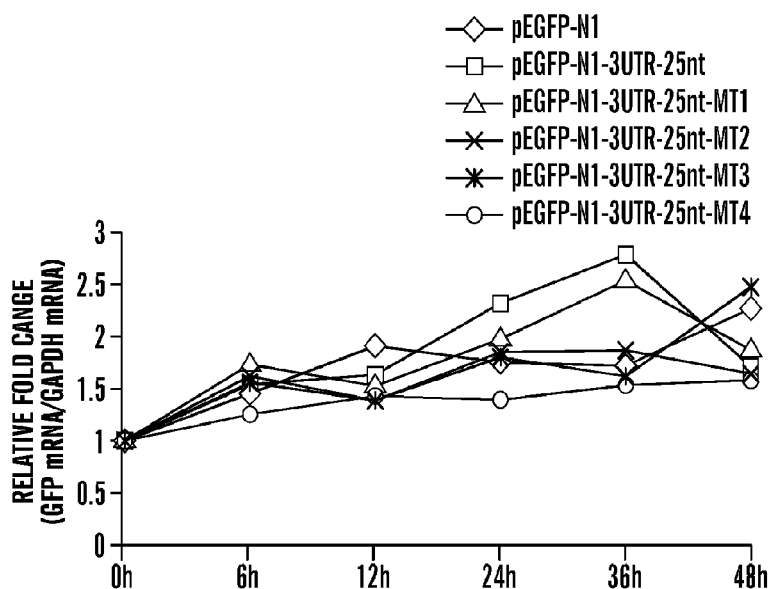
FIG. 6A-FIG. 6C shows experimental results in the form of line graphs, photographs of Western blots and bar graphs. The results indicate the effect of miR-1289 expression on the EGFP mRNA and protein levels.
Figure 6B:
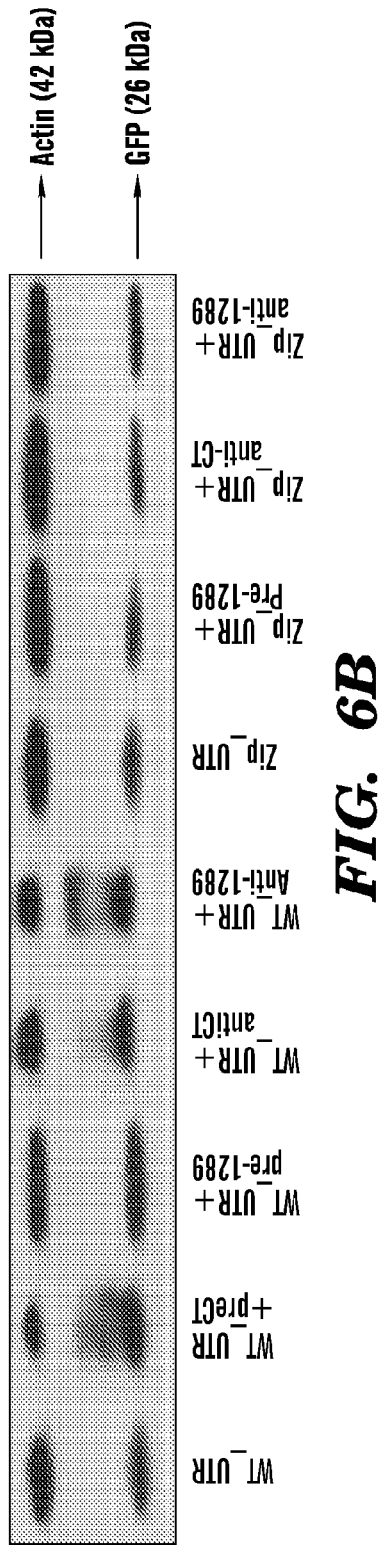
Figure 6C:
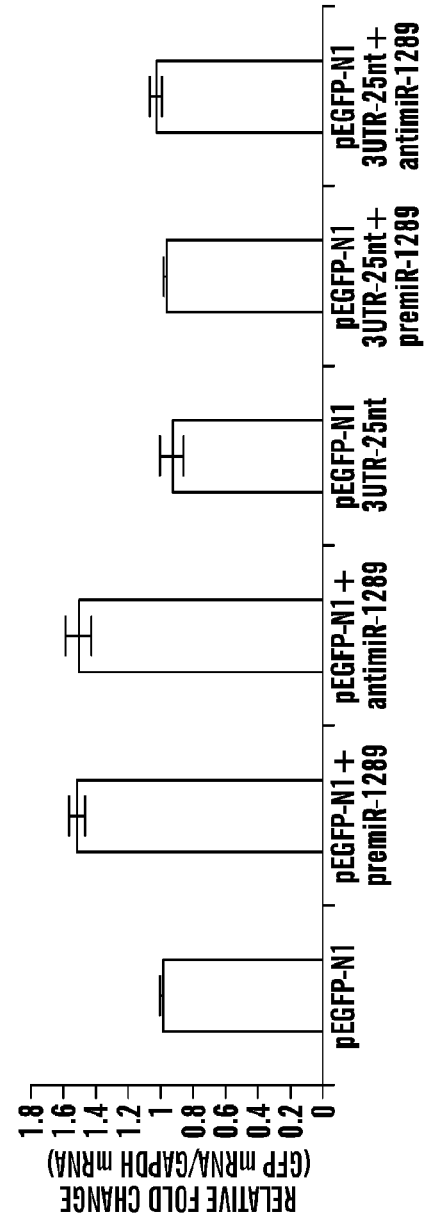

Investigation was then made into the presence of miR-1289 target sites within 3'UTRs of the top 50 enriched mRNAs. 14 of these mRNAs were found to exhibit computationally predicted target sequences in their 3'UTR (FIG. 11). To test whether decreased uptake of the reporter mRNA with a mutant zip code into MVs was due to increased degradation of mRNA within cells, RT-PCRs was also performed for the cellular EGFP mRNA. As shown in FIG. 6A, there was no significant difference in levels of mutant and wild-type EGFP mRNAs in cells over a 48 hour period of time. In addition, in cells co-transfected with pre-miR-1289 and pEGFP-N1-3UTR-25nt, EGFP expression was not downregulated indicating that there was no inhibition of translation in these conditions (FIG. 6B). qRT-PCR reactions also showed that cellular mRNA levels of pEGFP-N1 3'UTR-25nt were not altered compared to control vector (FIG. 6C). Taken together, the data indicated that miR-1289 does not inhibit translation of the EGFP-N1 3'UTR-25nt mRNA, but rather may provide a means of novel posttranscriptional gene silencing mechanism by mediating the transfer of this mRNA into MVs.

The MV mRNA enrichment assay findings suggest that the presence of both the core "CTGCC" region and the miR-1289 binding site promote targeting of mRNA into MVs. To determine the extent to which these two elements are present within enriched and reduced sets of mRNAs in MVs, the 3' UTR sequences of the top 50 enriched and 50 reduced mRNAs in MVs was searched, as compared to GBM cells for the presence of these elements. Surprisingly, among the enriched mRNAs set, the presence of both elements had more than twice the frequency as among the reduced mRNAs set (Table 3).

TABLE 3

Ratio of mRNAs with core sequence and/or miR-1289 binding site

|  | Enriched | | Reduced | |
| --- | --- | --- | --- | --- |
| Only core sequence "CTGCC" | 34 | 68% | 19 | 38% |
| Only miR1289 binding site | 14 | 28% | 7 | 14% |
| miR1289 binding site + CTGCC | 13 | 26% | 6 | 12% |
| Total | 50 | 100% | 50 | 100% |

Since the previous zip code studies on β-actin suggested the possible role of stem loop structures [18], analysis was performed to determine whether the 25 nt sequence predicts a stem loop structure. The mFold web server search predicted that this 25 nt putative zip code sequence can assume a stem loop configuration. Interestingly, the core "CTGCC" sequence and part of the miR-1289 binding sites are predicted to be located in this loop structure (FIG. 8). The secondary structures of the four mutant sequences generated in this study were then analyzed and compared using mFold (FIG. 8). In comparing the fold enrichment of the reporter mRNA in MVs:cells, it appears that the presence of both the "CTGCC" core sequence and part of the miR-1289 binding site on the loop are critical to sustain the 2-fold mRNA enrichment (Table 4).

TABLE 4

Relative fold enrichments of the zip
code and its mutated version in MVs

| Sequence | Fold | CTGCC | miR-1289 | loop |
|---|---|---|---|---|
| pEGFP-N1-3UTR-25nt (Zipcode) | ~2.1 | + | + | + |
| pEGFP-N1-3UTR-25nt -MT1 | ~0.95 | − | + | − |
| pEGFP-N1-3UTR-25nt -MT2 | ~1 | − | + | + |
| pEGFP-N1-3UTR-25nt -MT3 | ~2 | + | − | + |
| pEGFP-N1-3UTR-25nt -MT4 | ~1.2 | + | − | − |
| pEGFP-N1-3UTR-25nt + premiR1289 | ~6 | + | ++ | + |
| pEGFP-N1-3UTR-25nt + antimiR1289 | ~0.5 | + | − | + |

Discussion

MVs were first described almost three decades ago by Trams et al. [19] as exfoliated vesicles with ectoenzyme activity. In recent studies, they have proven valuable as a "transparent window" of biomarkers to monitor the disease status in patients, including cancer and neurodegenerative disorders [20]. Research in recent years has also pointed out their "cargo role" as a communication tool between cells in the horizontal transfer of RNAs and proteins between cells [5, 6, 3, 21]. Despite these intensive studies, the molecular mechanism by which genetic materials are uploaded into and transferred by MVs is still unknown, although for shedding MVs RNA incorporation may have parallels with retrovirus budding from the plasma membrane [22]. The present study has shown that there is a zip code-like 25 nt sequence which contains a short "CTGCC" core domain on a stem loop structure and carries a miR-1289 binding site in the 3' UTRs of many of the most enriched mRNAs in MVs derived from human primary GBM cells and as well as melanoma cells. Furthermore, it has shown that miR-1289 binds directly to this zip code and orchestrates transfer mRNAs into MVs. This zip code sequence can be used to increase the levels of mRNAs into MVs.

Studies focusing on intracellular mRNA localization started two decades ago and specific localization of mRNAs have been shown in various organisms and systems: budding yeast, Drosophila, Xenopus, and in mammalian cells including fibroblasts, oligodendrocytes and neurons [23, 14, 24]. One type of these mRNA-protein complexes is found in cytoplasmic foci called processing bodies (P-bodies), which contain untranslated mRNAs and can serve as sites of mRNA degradation or storage [25]. Another study provided a link between miRNA function and mammalian P-bodies, as argonaute proteins were found to be localized to mammalian P-bodies in a miRNA dependent manner [26]. miRNAs typically associate with a complex of proteins that includes a member of the Argonaute (AGO) family with which they form the RNA-induced silencing complex (RISC) including target mRNAs [27,28]. In addition, Gibbings et al. showed a novel cellular mRNA storage site called GW-bodies containing GW182 and AGO2 proteins which is distinct from P-bodies and can serve as a novel storage depot for miRNA-mRNA loading [29]. These studies together with the observations reported herein suggested that not only P- or GW-bodies, but also MVs may be sites of miRNA-mRNA interaction involved in suppressing mRNA translation in the host cell. It remains to be investigated whether the zip code-like sequence identified herein might also participate in mRNA transport into P- or GW-bodies. Another interesting question which will require further investigation is whether other members of the RISC machinery are involved in the mRNA enrichment in MVs mediated by a zip code-like sequence.

One of the earliest studies on regulatory function of 3' UTRs in determining the cellular localization and translation of mRNAs came from analysis of chicken β-actin mRNA. A 54 nt sequence in the 3' UTR of β-actin mRNA was found to be essential and sufficient for mRNA localization to the cell periphery [30, 31]. This sequence also contains a hexanucleotide sequence (ACACCC), which is conserved and also forms a stem-loop structure in β-actin mRNA in other species [18]. This study also suggested that the functional protein-RNA interactions may depend on this stem-loop secondary structure. Interestingly, the zip code-like sequence described herein is also predicted to form a stem-loop secondary structure. The mutation analysis showed that the core sequence of this zip code, "CTGCC" is indispensable for increased transport of the reporter EGFP mRNAs into MVs and functions most efficiently within the context of the loop structure. The findings reported herein suggest that the presence of both the CTGCC core sequence on the loop structure and the miR-1289 binding site in the 3' UTR have a critical role in increasing the incorporation of mRNAs into MVs.

Recent studies provided similarities between biogenesis of shed MVs and retrovirus budding, in particular, targeting signals such as oligomeric proteins with plasma membrane anchors can deliver proteins into MVs [22, 32]. It remains to be investigated whether the zip code-like sequence identified in the present study can act as a regulatory cis-element incorporated into the RISC complex with Ago 2 to direct some mRNAs into MVs or serves as a sorting signal or anchor to plasma membrane proteins involved in MV biogenesis.

Cancer MVs studies in recent years have raised interesting questions as to why tumor cells would seek to load particular mRNAs or miRNAs into MVs. Possible explanations are that mRNAs enrichment in MVs serves as "rubbish containers" whereby mRNAs are eliminated from the host cells through the miRNA-mRNA-RISC machinery, or that they serve as "storage containers" in which mRNAs are localized and transferred to other cells where they can be translated into proteins. The latter scenario seems to be very logical for tumors cells which express oncogenic mRNAs and proteins, such as for EGFRvIII in MVs which can be transferred to and active in recipient cells [5-7]. Perhaps, this storage mechanism is used to quickly initiate protein translation in recipient neighboring cells as a message of cancer transformation. Since MVs can also contain tumor suppressor miRNAs, it seems also possible that tumor cells may try to get rid of those miRNAs by transferring them in MVs. So, MV-mediated elimination or transfer of mRNAs and/or miRNAs could be used by tumor cells depending on the requirements of cellular conditions involved in tumor growth. In this study, based on the possible cancer-associated role(s) of the top four most enriched mRNAs in MVs released from GBM cells, it seems possible that cancer cells transfer these mRNAs to the other cells in which their translation might be promote tumorigenesis.

Among the four MV-enriched mRNAs within GBM vesicles are those corresponding to genes MDK, COX8C, GALR3 and LOC653602, the first three encode known cancer-associated proteins. One of these enriched mRNAs is the Galanin receptor 3 (GALR3). Berger et al. [33] has shown that both GAL and its specific receptors are elevated in human gliomas, as compared to normal tissue. Based on these findings, it seems highly likely that these receptors are cancer-related and transfer via MVs would support tumor growth through increasing an immortalized profile in surrounding stromal cells. This mRNA was increase 50% in MVs derived from HEK-293 cells when the cells were transfected with pre-miR1289, consistent with the studies described herein using the reporter zip code mRNA.

Another of the most enriched mRNA in MVs found in the microarray was Midkine (MK or MDK), also known as neurite growth-promoting factor 2, which promotes cell proliferation, cell migration and angiogenesis in several types of cancer in culture and in vivo [34]. The cancer-related activity of MK mRNA and protein expression are frequently elevated in many types of human carcinomas, including breast, lung, esophageal, stomach, colorectal, liver, ovary prostate and urinary bladder carcinomas, as well as GBMs, neuroblastomas and Wilms' tumors [35-42]. However, the MDK mRNA does not carry this zip code and was not enriched in MVs derived from HEK-193 cells after transfection with pre-miR1289.

The 25 nt zip code-like sequence elucidated in these studies corresponds to sequences within the 3' UTRs of many of the mRNAs enriched in MVs from GBM cells (FIG. 1). Therefore, the sequence is not specific to one type of mRNA, but rather appears to represent a consensus sequence present in the 3' UTRs of a number of mRNAs enriched in tumor cell MVs. The herein disclosed experimental analysis showed that this 25 nt zip code-like sequence results in 2-fold mRNA enrichment in MVs, as compared to their cells of origin using a reporter mRNA. This enrichment was only seen in two cell types and may not be a universal mechanism. The MV isolation strategy would result in the harvesting of a variety of MV subtypes, including exosomes, shed MVs, and microparticles. Hence, it may be possible that the actual enrichment level in a subtype of MVs is much higher.

Discovery of a zip code-like sequence which can target mRNAs to MVs is important in many different aspects of MV dynamics. MVs are now being considered as one of the essential intercellular communication tools and little is known about the basic biologic mechanisms underlying this form of communication. Understanding the physiological processes behind the transfer of RNA messages has broad ranging implications, from developmental studies to tumorigenesis, from cancer gene therapy to immunological studies (11, 12). An important aspect of this miRNA/mRNA transfer dynamic is that in some cases it may be a means of a cell eliminating and thereby decreasing translation of a specific protein, while in other cases it may serve to transmit miRNAs or mRNAs to recipient cells where they are active and modulate their phenotype. One potential approach for cancer gene therapy could be that this sequence can incorporated into the 3' UTR of therapeutic RNAs (including mRNAs, shRNAs and non-coding regulatory RNAs) to enrich them in MVs, which, in turn, can serve as vehicles to deliver them to cells in vivo through on-site donor cells or through injection of loaded MVs.

Materials and Methods
Cell Culture.

HEK-293T cells (obtained from Dr. Maria Calos, Stanford University) were cultured in Dulbecco's Modified Eagle Medium (DMEM, Cellgro, Mediatech Inc., Manassas, Va.) containing 10% fetal bovine serum (FBS), 100 IU/ml penicillin and 100 µg/ml streptomycin. Cells are incubated at 37° C. in a 5% $CO_2$ atmosphere. Cells were determined to be mycoplasma negative by testing with a mycoplasma detection kit (MycoAlert® *Mycoplasma* Detection Assay: Lonza, Rockland, Me.).

Transfection of HEK-293T Cells and Microvesicle Isolation.

Cultures of HEK-293T cells (75-80% confluent) were transfected with 7 µg pEGFP-N1 original or derived plasmids per each 200 mm plate with Lipofectamine 2000 (Invitrogen, 11668-019), according to manufacturer's protocol. Six hours later, transfection media was removed and replaced with DMEM containing 5% MV-free FBS. Microvesicle-free FBS is obtained after the ultracentrifugation and filtration process [5]. Three days after transfection, MVs were isolated from a total of 39 ml cell media from two plates through serial centrifugation: initial centrifugation was done at 300 g for 15 minutes followed by 16000 g for 30 minutes. Then, the supernatant was filtered through 0.22 µm filters (Millex, Millipore, Billerica, Mass.) into Beckman Quick seal tubes. Finally, ultracentrifugation was performed at 110,000 g for 90 minutes using a 70Ti rotor (Beckman Coulter, Brea, Calif.). Microvesicles were resuspended in 50 µl twice-filtered 1×PBS.

miRNA Overexpression and Inhibition.

Precursory and inhibitory miRNAs used for the experiments were as follows: pre-miR-1289 (Ambion, Foster City, Calif.; AM17100), pre control 1 (AM17110), anti-miRNA-1289 (AM17000) and anti-miR miRNA inhibitors—negative control 1 (AM17010). Both pre-miR and anti-miRs were used at 50 nM final concentration for co-transfection experiments.

Total RNA Isolation, Reverse Transcription and Real-Time qPCR.

Total RNA was isolated from both cell pellets and MVs using a miRvana isolation kit (Ambion), according to manufacturer's protocol. Upon elution of RNA, it was treated with 1 µl 2 U DNaseI (Ambion) in 30 µl of total reaction for 30 minutes at 37° C. to eliminate any residual DNA. Following the RNA isolation, complementary DNA was generated using Omniscript RT kit-50 (Qiagen, Valencia, Calif.) using 100 ng of total RNA from MVs or 1 µg of total RNA from cell pellets, according to manufacturer's recommendations. mRNA levels were quantified with Applied Biosystems 7000 series quantitative PCR. GAPDH mRNA was used for normalization purposes. The primers used in this study were as follows:

```
GALR3-Forward:
                                    (SEQ ID NO: 39)
5'CATGTACGCCAGCAGCTTTA, GALR3-Reverse:
                                    (SEQ ID NO: 40)
5'-ACGGTGCCGTAGTAGCTGAG;

MDK-Forward:
                                    (SEQ ID NO: 41)
5'-CGGTCGCCAAAAAGAAAGAT, MDK-Reverse:
                                    (SEQ ID NO: 42)
5'-GGCTCCAAACTCCTTCTTCC, GAPDH-Forward:
                                    (SEQ ID NO: 43)
5'-GAAGGTGAAGGTCGGAGT, GAPDH-Reverse:
                                    (SEQ ID NO: 44)
5'-GAAGATGGTGATGGGATTTC,
and EGFP-Forward:
                                    (SEQ ID NO: 45)
5'-CCTGAAGTTCATCTGCACCA
and
```

```
                            -continued
EGFP-Reverse:
                                        (SEQ ID NO: 46)
           5'-GGTCTTGTAGTTGCCGTCGT.
```

Molecular Cloning and Site Specific Mutagenesis.

For microsomal enrichment assays, pEGFP-N1 (Clontech) was used as the parental vector. The 3' UTR of EGFP was replaced with the putative 25 nt zip code at the Afl-2 and Not-1 sites and mutants of this sequence were inserted at the same sites (FIG. 10). In order to maintain mRNA stability, part of the 3' UTR of the original construct was maintained to retain the SV40 polyA addition site. The 3' UTRs of pEGFP-N1-3UTR-25nt, pEGFP-N1-NO3UTR, and pEGFP-N1-3UTR-25nt-MT4 inserts were generated by oligonucleotide annealing, as described [43]. These oligonucleotide sequences as follows:

```
pEGFP-N1-3UTR-25nt
                                        (SEQ ID NO: 47)
(5'-GGCCGCACCCTGCCGCCTGGACTCCGCCTGTACAAATAAAGCAATA
GCATCACAAATTTCACAAATAAAGCATTTTTTTCACTGCC-3'), pEGFP-N1-NO3UTR
                                        (SEQ ID NO: 48)
(5'GCCGCACAAATAAAGCAATAGCATCACAAATTTCACAAATAAAGCAT
TTTTTTCACTGCC-3'),
and pEGFP-N1-3UTR-25nt-MT4
                                        (SEQ ID NO: 49).
(5'-GCCGCACCCTGCCGCCCTGATCGCGCCTGTACAAATAAAGCAATA
GCATCACAAATTTCACAAATAAAGCATTTTTTTCACTGCC-3'
``` pEGFP-N1-3UTR-25nt-MT1, pEGFP-N1-3UTR-25nt-MT2 and pEGFP-N1-3UTR-25nt-MT3 plasmids were derived from pEGFP-N1-3UTR-25nt using Quickchange site-directed mutagenesis kit (Stratagene, Santa Clara, Calif.). Primer sequences used in site directed mutagenesis reactions as follows:

```
MT1forward:
                                        (SEQ ID NO: 50)
5'-CAAGTAAAGCGGCCGCACCGCATGGCCTGGACTCCGCCTGTAC MT1reverse:
                                        (SEQ ID NO: 51)
5'-GTACAGGCGGAGTCCAGGCCATGCGGTGCGGCCGCTTTACTTG MT2forward:
                                        (SEQ ID NO: 52)
5'-CAAGTAAAGCGGCCGCACCACTTAGCCTGGACTCCGCCTGTAC MT2reverse:
                                        (SEQ ID NO: 53)
5' GTACAGGCGGAGTCCAGGCTAAGTGGTGCGGCCGCTTTACTTG MT3forward:
                                        (SEQ ID NO: 54)
5'-GCACCCTGCCGCCTGGATCAAGCCTGTACAAATAAAGCAATAGC MT3reverse:
                                        (SEQ ID NO: 55)
5'-CTATTGCTTTATTTGTACAGGCTTGATCCAGGCGGCAGGGTGCGG.
```

Western Blots.

Three days after transfection, HEK-293T cells were rinsed with 1×PBS and harvested, and total proteins were separated by pre-cast NuPAGE 4-12% Bis-Tris (Invitrogen, Carlsbad, Calif.) polyacrylamide gel electrophoresis. Then proteins were transferred onto nitrocellulose membranes; membranes were blocked with 5% nonfat dry milk in PBS containing 0.05% Tween 20 [44] overnight at 4° C. The antibodies used were: monoclonal EGFP (1:5000; Invitrogen; 33-2600) and β-actin (1:5000; Sigma, St. Louis, Mo.; A5356). Bands were visualized using the ECL system according to instructions provided by the supplier (Amersham, Buckinghamshire, UK).

Luciferase miRNA Target Reporter Assay.

For the validation of the miR-1289 binding site in the putative MV zip code, the pMir-Report system (Ambion, AM5795) was used as described [45]. In this system, the 3' UTR of firefly luciferase (Fluc) gene was replaced either with the putative MV zip code or the MT1289 mutated version of this zip code. DNA oligonucleotides were synthesized as sense and antisense templates of the 25 nt sequence and the mutant sequence. Then, they were annealed and cloned into pMir-Report between the HindIII and SpeI sites. The oligonucleotides used in these studies were as follows:

```
25 nt-zip code-UTR
                                        (SEQ ID NO: 56))
(5'-CTAGTACCCTGCCGCCTGGACTCCGCCTGTA-3'

25 nt-zip code-MT4:
                                        (SEQ ID NO: 57))
(5'-CTAGTACCCTGCCGCCCTGATCGCGCCTGTA-3'.
```

HEK-293T cells were co-transfected with pMir-Report vectors and either pre-miR-1289 or pre-miR negative control 1. Two days after transfection, cells were lysed and the luciferase activity was measured. Another plasmid with a *Renilla* luciferase (Rluc) expression cassette was co-transfected and used for normalization [45].

Multiple Sequence Alignment and Zip Code Scanning.

The list of 50 most enriched and most reduced mRNAs in MVs as compared to GBM cells were generated from microarray data of Skog et al. [5]. The 3' UTR sequences of the top enriched 20 genes were aligned using the multiple sequence alignment tool ClustalW (Clustal W2) under the following conditions: fast alignment method, gap open 10, gap extend 0.2, and DNA weight matrix ClustalW. In addition, for deep alignment a slow alignment method was used. In order to eliminate false negative hits, polyA sequences in the 3' ends of the sequences were excluded. Sequence similarities were found through pairwise alignment option of the BLAST. The nucleotide blast (blastn) program was used with minimum hit length of 7 nt.

MicroRNA Binding Site Predictions.

miRNA targeting sequences within the 25 nt putative MV zip code were checked using miRBase. Predicted target transcripts of miR-1289 were collected and combined from three different miRNA databases: TargetScanHuman, microRNA.org, and miRWalk. In addition, blastn was used to detect additional similarities which were 7 bp or longer.

REFERENCES

1. Cocucci, E, Racchetti, G and Meldolesi, J (2009). Shedding microvesicles: artefacts no more. *Trends Cell Biol* 19: 43-51.
2. Ratajczak, J, Wysoczynski, M, Hayek, F, Janowska-Wieczorek, A and Ratajcz M Z (2006). Membrane-derived microvesicles: important and underappreciated mediators of cell-to-cell communication. *Leukemia* 20: 1487-1495.
3. Al-Nedawi, K, Meehan, B and Rak J (2009). Microvesicles: messengers and mediators of tumor progression. *Cell Cycle* 8: 2014-2018.

4. Ratajczak, J, Miekus, K, Kucia, M, Zhang, J, Reca, R, Dvorak, P et al. (2006). Embryonic stem cell-derived microvesicles reprogram hematopoietic progenitors: evidence for horizontal transfer of mRNA and protein delivery. *Leukemia* 20: 847-856.
5. Skog, J, Würdinger, T, van Rijn, S, Meijer, D, Gainche, L, Curry, W T J et al. (2008). Glioblastoma microvesicles transport RNA and protein that promote tumor growth and provide diagnostic biomarkers. *Nat Cell Biol* 10: 1470-1476.
6. Valadi, H, Ekström, K, Bossios, A, Sjöstrand, M, Lee, J J and Lötvall, J O (2007). Exosome-mediated transfer of mRNAs and microRNAs is a novel mechanism of genetic exchange between cells. *Nat Cell Biol* 9: 654-659.
7. Al-Nedawi, K, Meehan, B, Micallef, J, Lhotak, V, May, L, Guha, A et al. (2008). Intercellular transfer of the oncogenic receptor EGFRvIII by microvesicles derived from tumour cells. *Nat Cell Biol* 10: 619-624.
8. van der Vos, K E, Balaj, L, Skog J and Breakefield X O (2011). Brain tumor microvesicles: Insights into intercellular communication in the nervous system. *Cell Mol Neurobiol* 31: 949-959.
9. Hendrix, A, Westbroek, W, Bracke, M and De Wever O (2010). An ex(o)citing machinery for invasive tumor growth. *Cancer Res* 70: 9533-9537.
10. Rak, J (2010). Microparticles in cancer. *Semin Thromb Hemost* 36: 888-906.
11. Alvarez-Erviti L, Seow Y, Yin H, Betts C, Lakhal S, Wood M J. (2011) Delivery of siRNA to the mouse brain by systemic injection of targeted exosomes. *Nat Biotechnol* 29: 341-345.
12. Zhuang X, Xiang X, Grizzle W, et al. (2011) Treatment of brain inflammatory diseases by delivering exosome encapsulated anti-inflammatory drugs from the nasal region to the brain. *Mol Ther* 19: 1769-1779.
13. Jansen, R P (2001). mRNA localization: message on the move. *Nat Rev Mol Cell Biol* 2: 247-256.
14. Martin, K C and Ephrussi, A (2009). mRNA localization: gene expression in the spatial dimension. *Cell* 136: 719-730.
15. Bartel, D P (2004). MicroRNAs: genomics, biogenesis, mechanism, and function. *Cell* 116: 281-297.
16. Erkan, E P, Breakefield, X O and Saydam, O (2011). miRNA signature of schwannomas: possible role(s) of "tumor suppressor" miRNAs in benign tumors. *Oncotarget* 2: 265-270.
17. Fabian, M C, Sonenberg, N and Filipowicz, W (2010). Regulation of mRNA Translation and Stability by microRNAs. *Annu Rev Biochem* 79: 351-379.
18. Ross, A F, Oleynikov, Y, Kislauskis, E H, Taneja, K L and Singer, R H (1997). Characterization of a beta-actin mRNA zip code-binding protein. *Mol Cell Biol* 17: 2158-2165.
19. Trams, E G, Lauter, C J, Salem, N and Heine, U (1981). Exfoliation of membrane ecto-enzymes in the form of micro-vesicles. *Biochim Biophys Acta* 645: 63-70.
20. Dowling, P and Clynes, M (2011). Conditioned media from cell lines: a complementary model to clinical specimens for the discovery of disease-specific biomarkers. *Proteomics* 11: 794-804.
21. Record, M, Subra, C, Silvente-Poirot, S. and Poirot, M. Exosomes as intercellular signalosomes and pharmacological effectors. *Biochem Pharmacol* 81: 1171-1182.
22. Shen, B, Wu, N, Yang, J M and Gould, S J (2011). Protein targeting to exosomes/microvesicles by plasma membrane anchors. *J Biol Chem* 286: 14383-14395.
23. Andreassi, C and Riccio, A (2009). To localize or not to localize: mRNA fate is in 3'UTR ends. *Trends Cell Biol* 19: 465-474.
24. Meignin, C and Davis, I (2010). Transmitting the message: intracellular mRNA localization. *Curr Opin Cell Biol* 22: 112-119.
25. Garneau, N L, Wilusz, J and Wilusz, C J (2007). The highways and byways of mRNA decay. *Nat Rev Mol Cell Biol* 8: 113-126.
26. Liu, J, Valencia-Sanchez, M A, Hannon, G J and Parker, R (2005). MicroRNA-dependent localization of targeted mRNAs to mammalian P-bodies. *Nat Cell Biol* 7: 719-723.
27. Kim, V N, Han, J and Siomi, M C (2009). Biogenesis of small RNAs in animals. *Nat Rev Mol Cell Biol* 10: 126-139.
28. Carthew, R W and Sontheimer, E J (2009). Origins and mechanisms of miRNAs and siRNAs. *Cell* 136: 642-655.
29. Gibbings, D J, Claudo, C, Erhardt, M and Voinnet, O (2009). Multivesicular bodies associate with components of miRNA effector complexes and modulate miRNA activity. *Nat Cell Biol;* 11: 1143-1149.
30. Kislauskis, E H, Li, Z, Singer, R H and Taneja, K L (1993). Isoform-specific 3'-untranslated sequences sort α-cardiac and β-cytoplasmic actin messenger RNAs to different cytoplasmic compartments. *J Cell Biol* 123: 165-172.
31. Kislauskis, E H, Zhu, X and Singer, R H (1994). Sequences responsible for intracellular localization of beta-actin messenger RNA also affect cell phenotype. *J Cell Biol* 127: 441-451.
32. Gan, X and Gould, S J (2011). Identification of an inhibitory budding signal that blocks the release of HIV particles and exosome/microvesicle proteins. *Mol Biol Cell* 22: 817-830.
33. Berger, A, Santic, R, Hauser-Kronberger, C, Schilling, F H, Kogner, P, Ratschek, M et al. (2005). Galanin and galanin receptors in human cancers. *Neuropeptides* 39, 353-359.
34. Kadomatsu, K (2005). The midkine family in cancer, inflammation and neural development. *Nagoya J Med Sci* 67: 71-82.
35. Tsutsui, J, Kadomatsu, K, Matsubara, S, Nakagawara, A, Hamanoue, M, Takao, S et al. (1993). A new family of heparin-binding growth/differentiation factors: increased midkine expression in Wilms' tumor and other human carcinomas. *Cancer Res* 53: 1281-1285.
36. Garver, R I, Chan, C S and Milner, P G (1993). Reciprocal expression of pleiotrophin and midkine in normal versus malignant lung tissues. *Am J Respir Cell Mol Biol* 9: 463-466.
37. Aridome, K, Tsutsui, J, Takao, S, Kadomatsu, K, Ozawa, M, Aikou, T et al. (1995). Increased midkine gene expression in human gastrointestinal cancers. *Jpn J Cancer Res* 86: 655-661.
38. Nakagawara, A, Milbrandt, J, Muramatsu, T, Deuel, T F, Zhao, H, Cnaan, A et al. (1995). Differential expression of pleiotrophin and midkine in advanced neuroblastomas. *Cancer Res* 55: 1792-1797.
39. O'Brien, T, Cranston, D, Fuggle, S, Bicknell, R and Harris, A L (1996). The angiogenic factor midkine is expressed in bladder cancer, and overexpression correlates with a poor outcome in patients with invasive cancers. *Cancer Res* 56: 2515-2518.

40. Mishima, K, Asa, I A, Kadomatsu, K, Ino, Y, Nomura, K, Narita, Y et al. (1997). Increased expression of midkine during the progression of human astrocytomas. *Neurosci Lett* 233: 29-32.
41. Konishi, N, Nakamura, M, Nakaoka, S, Hiasa, Y, Cho, M, Uemura, H et al. (1999). Immunohistochemical analysis of midkine expression in human prostate carcinoma. *Oncology* 57: 253-257.
42. Balaj, L, Lessard, R, Dai, L, Cho, Y-J, Pomeroy, S L, Breakefield, X O et al. (2011). Tumour microvesicles contain retrotransposon elements and amplified oncogene sequences. *Nat Commun* 2: 180.
43. Cheng, A M, Byrom, M W, Shelton, J and Ford, L P (2005). Antisense inhibition of human miRNAs and indications for an involvement of miRNA in cell growth and apoptosis. *Nucleic Acids Res* 33: 1290-1297.
44. Saydam, O, Glauser, D L, Heid, I, Turkeri, G, Hilbe, M, Jacobs, A H et al. (2005). Herpes simplex virus 1 amplicon vector-mediated siRNA targeting epidermal growth factor receptor inhibits growth of human glioma cells in vivo. *Mol Ther* 12: 803-812.
45. Saydam, O, Senol, O, Würdinger, T, Mizrak, A, Ozdener, G B, Stemmer-Rachamimov, A O et al. (2011). miRNA-7 attenuation in schwannoma tumors stimulates growth by upregulating three oncogenic signaling pathways. *Cancer Res* 17: 852-861.

Example 2

Figure 12:
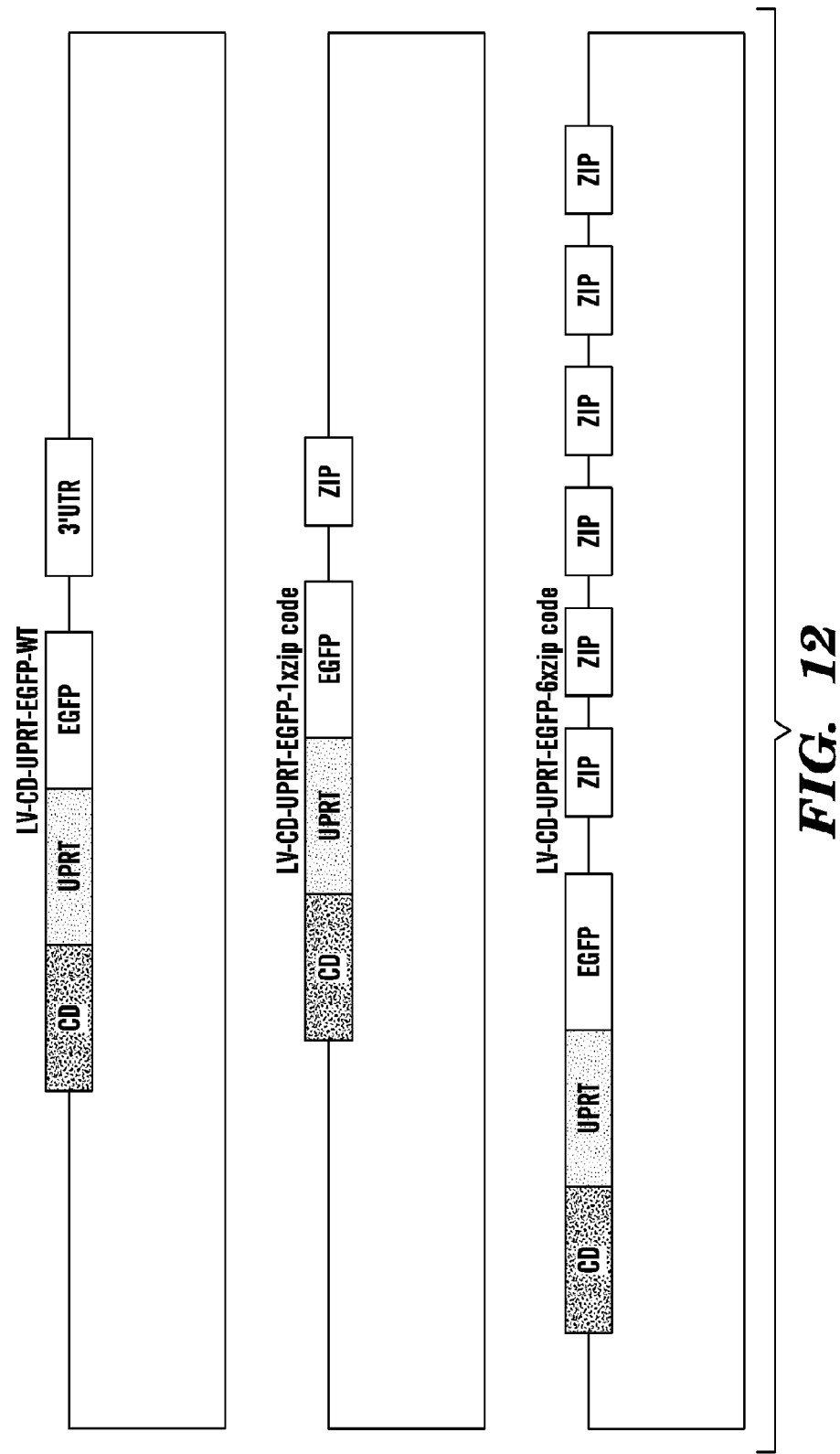
FIG. 12 shows lentiviral constructs expressing suicide gene therapy genes CD-UPRT-EGFP fused to 1× zipcode, or 6× zipcode. In order to see whether zipcode sequences are functional in vivo, three lentiviral constructs were generated as shown. CD-UPRT-EGFP coding sequences from the clones described in (Mizrak et al., Mol Ther. 2013 January; 21(1): 101-8) were transferred into lentiviral constructs carrying wt (wild-type-original 3'UTR) or 1× zipcode or 6× zipcode sequences (Bolukbasi et al., 2012) and the resulting plasmids express CD-UPRT-EGFP mRNA fused to zipcode(s), followed by a polyA addition site and referred to here as LV-CD-UPRT-EGFP WT or 1× zipode or 6× zipcode.
Figure 13:
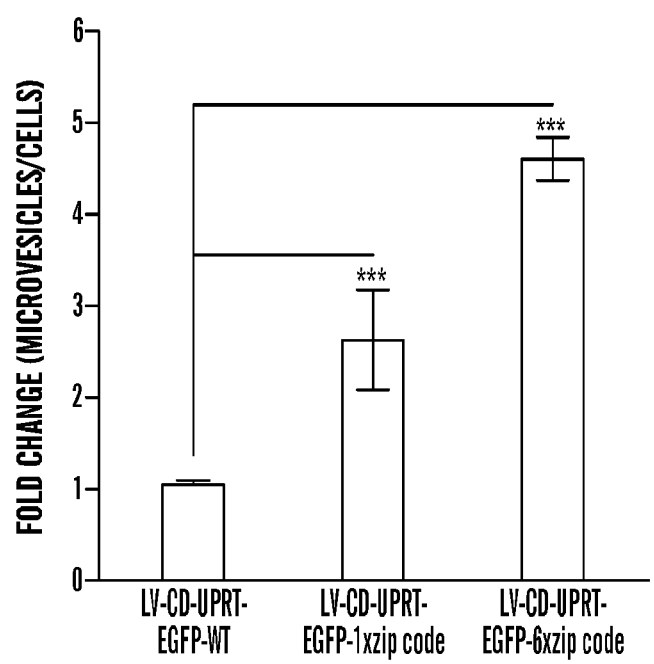
FIG. 13 shows enrichment of CD-UPRT-EGFP mRNAs in MVs. Human embryonic kidney-293T (HEK-293T) cells were transfected with either LV-CD-UPRT-EGFP-WT or LV-CD-UPRT-EGFP-1× zipcode or LV-CD-UPRT-EGFP-6× zipcode and 72 hours later, MVs and cells were harvested. qRT-PCR was performed for CD-UPRT and GAPDH mRNAs. MVs collection from medium and RT-PCRs were performed as described (Mizrak et al., Mol Ther. 2013 January; 21(1): 101-8). The data were normalized to the level of GAPDH mRNA in each sample. This experiment was performed in triplicate, the values are expressed as mean±SD using Student's t-test; ***P<0.001.

The experiments presented herein, make possible a novel approach to selectively packaging therapeutic RNAs into extracellular vesicles. Such packaging would typically be done in vitro for any experimental or clinical applications by enriching selective RNAs in extracellular vesicles in vitro. This is achieved by incorporating the zipcode described herein in mRNAs, miRNA precursors and other non-coding RNAs to increase their content in extracellular vesicles. Results of experiments shown in FIGS. 12 and 13 further indicate that when the zipcodes are incorporated into the 3'UTR of cytosine deaminase (CD)-uracil phosphoribosyl-transferase (CD-UPRT) mRNAs, the enrichment of these mRNAs in extracellular vesicles were increased significantly as compared with the original wt construct.

What is claimed:

1. An in vitro method of producing a microvesicle preparation enriched for a specific desired RNA sequence, comprising:
   a) transfecting cells in vitro with a DNA molecule in expressible form, comprising two or more copies of a first nucleic acid sequence 5'-ACCCTGCCGCCTG-GACTCCGCCTGT-3' (SEQ ID NO: 22), operably linked to a second, heterologous nucleic acid sequence encoding a specific desired RNA sequence, under conditions suitable for expression of an RNA transcript; and
   b) isolating microvesicles generated by the transfected cells of step a);
to thereby produce a microvesicle preparation enriched for the specific desired RNA sequence.

2. The method of claim 1, wherein the DNA molecule is in the context of an expression vector.

3. The method of claim 1, wherein the first nucleic acid sequence is located 3' of the second nucleic acid sequence.

4. The method of claim 1, wherein the first nucleic acid sequence is located 5' of a poly adenylation site.

5. The method of claim 1, further comprising transfecting the cells with a construct capable of expressing a pre-miR-1289 RNA under conditions suitable for expression.

6. The method of claim 1, wherein the specific RNA sequence is selected from the group consisting of a mRNA, a shRNA, and a regulatory ncRNA.

7. The method of claim 1, wherein transfection is by lipofection.

8. The method of claim 1, wherein the cells are primary cells or a continuous cell line.

9. The method of claim 8, wherein the cells are dendritic cells.

10. An in vitro method of producing a microvesicle preparation enriched for a specific RNA sequence, comprising:
    a) transfecting cells in vitro with:
       (i) a DNA molecule in expressible form, comprising a first nucleic acid sequence 5'-ACCCTGCCGCCTG-GACTCCGCCTGT-3' (SEQ ID NO: 22), operably linked to a second, heterologous nucleic acid sequence encoding the specific RNA sequence; and
       (ii) a construct capable of expressing a pre-miR-1289 RNA;
    under conditions suitable for expression; and
    b) isolating microvesicles generated by the transfected cells of step a);
to thereby produce a microvesicle preparation enriched for the specific RNA sequence.

11. The method of claim 1, wherein the first nucleic acid sequence further comprises one or more copies of 5'-ACCCTGCCGCCTGGATCAAGCCTGT-3' (SEQ ID NO: 38).

12. An in vitro method of producing a microvesicle preparation enriched for a specific desired RNA sequence, comprising:
    a) transfecting cells in vitro with a DNA molecule in expressible form, comprising a first nucleic acid sequence comprising 5'-ACCCTGCCGCCTG-GACTCCGCCTGT-3' (SEQ ID NO: 22) and 5'-AC-CCTGCCGCCTGGATCAAGCCTGT-3' (SEQ ID NO:

38), operably linked to a second, heterologous nucleic acid sequence encoding the specific desired RNA sequence, under conditions suitable for expression of an RNA transcript; and b) isolating microvesicles generated by the transfected cells of step a);

to thereby produce a microvesicle preparation enriched for the specific desired RNA sequence.

\* \* \* \* \*

SEQUENCE LISTING

```
<160> NUMBER OF SEQ ID NOS: 95

<210> SEQ ID NO 1
<211> LENGTH: 26
<212> TYPE: DNA
<213> ORGANISM: Homo sapiens

<400> SEQUENCE: 1
ggcccacgcc ctccctctcc caggcc                                    26

<210> SEQ ID NO 2
<211> LENGTH: 56
<212> TYPE: DNA
<213> ORGANISM: Homo sapiens

<400> SEQUENCE: 2
gctaggcctg aggtgagata gaattgctcc atcctatgcc caggaggcct gcgtgg    56

<210> SEQ ID NO 3
<211> LENGTH: 51
<212> TYPE: DNA
<213> ORGANISM: Homo sapiens

<400> SEQUENCE: 3
tgaacagctg ttaacgtcca aaaactttc agaaaaagct gtgttttgt t           51

<210> SEQ ID NO 4
<211> LENGTH: 25
<212> TYPE: DNA
<213> ORGANISM: Homo sapiens

<400> SEQUENCE: 4
accctgccgc ctggactccg cctgt                                     25

<210> SEQ ID NO 5
<211> LENGTH: 26
<212> TYPE: DNA
<213> ORGANISM: Homo sapiens

<400> SEQUENCE: 5
gggccaccct caccgtctgc ctcaga                                    26
```

<210> SEQ ID NO 6
<211> LENGTH: 36
<212> TYPE: DNA
<213> ORGANISM: Homo sapiens

<400> SEQUENCE: 6
atcccaacag gccctggcag cgtctggact tgtgta                                    36

<210> SEQ ID NO 7
<211> LENGTH: 41
<212> TYPE: DNA
<213> ORGANISM: Homo sapiens

<400> SEQUENCE: 7
atgtagaagc ctgtctctgt acctctaact ggcagcaagt t                              41

<210> SEQ ID NO 8
<211> LENGTH: 51
<212> TYPE: DNA
<213> ORGANISM: Homo sapiens

<400> SEQUENCE: 8
caagtgctcc ttagttttta aatacatttt gagattaact ggaaacttga a                   51

<210> SEQ ID NO 9
<211> LENGTH: 49
<212> TYPE: DNA
<213> ORGANISM: Homo sapiens

<400> SEQUENCE: 9
agtggaaagt cacctacagg actgggccgg gcccagggcc tctggcttc                      49

<210> SEQ ID NO 10
<211> LENGTH: 57
<212> TYPE: DNA
<213> ORGANISM: Homo sapiens

<400> SEQUENCE: 10
aatccgaatt cttccagccc agcttcccgg gctctgtcct ccatatcgaa taataat             57

<210> SEQ ID NO 11
<211> LENGTH: 52
<212> TYPE: DNA
<213> ORGANISM: Homo sapiens

<400> SEQUENCE: 11
ggccccgggt gggcgcgagt cgctttgtat catcaataaa ttatttaacg gg                  52

<210> SEQ ID NO 12
<211> LENGTH: 29
<212> TYPE: DNA
<213> ORGANISM: Homo sapiens

<400> SEQUENCE: 12
cctcggtgct ctgccccatg ctgggagga                                            29

<210> SEQ ID NO 13

<400> SEQUENCE: 13

000

```
<210> SEQ ID NO 14
<211> LENGTH: 36
<212> TYPE: DNA
<213> ORGANISM: Homo sapiens

<400> SEQUENCE: 14
acagcttatt ccagagggag gcttggatca gcacct                                    36

<210> SEQ ID NO 15
<211> LENGTH: 32
<212> TYPE: DNA
<213> ORGANISM: Homo sapiens

<400> SEQUENCE: 15
ccctgctgcc cctgctgccc ctgctctgtc cc                                        32

<210> SEQ ID NO 16
<211> LENGTH: 26
<212> TYPE: DNA
<213> ORGANISM: Homo sapiens

<400> SEQUENCE: 16 gggggggccct gctcgcccct cgccag                                              26

<210> SEQ ID NO 17
<211> LENGTH: 43
<212> TYPE: DNA
<213> ORGANISM: Homo sapiens

<400> SEQUENCE: 17
tccgggtgac cccacagggc ctttccaagc ccccatttga gct                            43

<210> SEQ ID NO 18
<211> LENGTH: 47
<212> TYPE: DNA
<213> ORGANISM: Homo sapiens

<400> SEQUENCE: 18
catgccctgt ggtcactgcg gttgccgccc ctaattgtgc caaaggc                        47

<210> SEQ ID NO 19
<211> LENGTH: 52
<212> TYPE: DNA
<213> ORGANISM: Homo sapiens

<400> SEQUENCE: 19
ggcccgcggc cgctcgctca ggctccgact cacgcaacga atcaggtgat cg                  52

<210> SEQ ID NO 20
<211> LENGTH: 42
<212> TYPE: DNA
<213> ORGANISM: Homo sapiens

<400> SEQUENCE: 20
ccaggcacag ggcccgcagt gctgggacca gagccagatg ca                             42

<210> SEQ ID NO 21
<211> LENGTH: 55
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
```

```
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (44)..(44)
<223> OTHER INFORMATION: a, c, t, g, unknown or other

<400> SEQUENCE: 21
anangcccnc ngggngnccct nctggctctg ccccaanctg gaantatgtt aatgg      55

<210> SEQ ID NO 22
<211> LENGTH: 25
<212> TYPE: DNA
<213> ORGANISM: Homo sapiens

<400> SEQUENCE: 22
accctgccgc ctggactccg cctgt                                       25

<210> SEQ ID NO 23
<211> LENGTH: 23
<212> TYPE: RNA
<213> ORGANISM: Homo sapiens

<400> SEQUENCE: 23
uggaguccag gaaucugcau uuu                                         23

<210> SEQ ID NO 24
<211> LENGTH: 20
<212> TYPE: RNA
<213> ORGANISM: Homo sapiens

<400> SEQUENCE: 24
acccugccgc cuggacuccg                                             20

<210> SEQ ID NO 25
<211> LENGTH: 22
<212> TYPE: RNA
<213> ORGANISM: Homo sapiens

<400> SEQUENCE: 25
ugaguuaggc cuuuugacuc ca                                          22

<210> SEQ ID NO 26
<211> LENGTH: 24
<212> TYPE: RNA
```

<213> ORGANISM: Homo sapiens

<400> SEQUENCE: 26
aggccgaagg ugccucagac uccg          24

<210> SEQ ID NO 27
<211> LENGTH: 23
<212> TYPE: RNA
<213> ORGANISM: Homo sapiens

<400> SEQUENCE: 27
cuucgccucc cuccaggacu cca           23

<210> SEQ ID NO 28
<211> LENGTH: 23
<212> TYPE: RNA
<213> ORGANISM: Homo sapiens

<400> SEQUENCE: 28
uuuccccuuc uucccugacu cca           23

<210> SEQ ID NO 29
<211> LENGTH: 23
<212> TYPE: RNA
<213> ORGANISM: Homo sapiens

<400> SEQUENCE: 29
gggucaggca gagagagacu ccc           23

<210> SEQ ID NO 30
<211> LENGTH: 23
<212> TYPE: RNA
<213> ORGANISM: Homo sapiens

<400> SEQUENCE: 30
uccucacuca agaucugacu cca           23

<210> SEQ ID NO 31
<211> LENGTH: 22
<212> TYPE: RNA
<213> ORGANISM: Homo sapiens

<400> SEQUENCE: 31
uucaugaaua uucaugacuc cu            22

<210> SEQ ID NO 32
<211> LENGTH: 23
<212> TYPE: RNA
<213> ORGANISM: Homo sapiens

<400> SEQUENCE: 32
guggcuccaa ccccaagacu ccc           23

<210> SEQ ID NO 33
<211> LENGTH: 23
<212> TYPE: RNA
<213> ORGANISM: Homo sapiens

<400> SEQUENCE: 33
ccaggaggcc ugcguggacu cac           23

<210> SEQ ID NO 34
<211> LENGTH: 22

```
<212> TYPE: RNA
<213> ORGANISM: Homo sapiens

<400> SEQUENCE: 34 gucccuacu cccuggacua gu                                            22

<210> SEQ ID NO 35
<211> LENGTH: 20
<212> TYPE: RNA
<213> ORGANISM: Homo sapiens

<400> SEQUENCE: 35
cuggcagcgu cuggacuugu                                              20

<210> SEQ ID NO 36
<211> LENGTH: 23
<212> TYPE: RNA
<213> ORGANISM: Homo sapiens

<400> SEQUENCE: 36
cugcccagcc acccuggacg uga                                          23

<210> SEQ ID NO 37
<211> LENGTH: 23
<212> TYPE: RNA
<213> ORGANISM: Homo sapiens

<400> SEQUENCE: 37
uuggagcgga ggccuggacu ucu                                          23

<210> SEQ ID NO 38
<211> LENGTH: 25
<212> TYPE: DNA
<213> ORGANISM: Homo sapiens

<400> SEQUENCE: 38
accctgccgc ctggatcaag cctgt                                        25

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
catgtacgcc agcagcttta                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acggtgccgt agtagctgag                                              20

<210> SEQ ID NO 41
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 41
cggtcgccaa aaagaaagat                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggctccaaac tccttcttcc                                                    20

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gaaggtgaag gtcggagt                                                      18

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gaagatggtg atgggatttc                                                    20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cctgaagttc atctgcacca                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggtcttgtag ttgccgtcgt                                                    20

<210> SEQ ID NO 47
<211> LENGTH: 86
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 47
ggccgcaccc tgccgcctgg actccgcctg tacaaataaa gcaatagcat cacaaatttc      60
acaaataaag catttttttc actgcc                                           86

<210> SEQ ID NO 48
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gccgcacaaa taaagcaata gcatcacaaa tttcacaaat aaagcatttt tttcactgcc      60

<210> SEQ ID NO 49
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gccgcaccct gccgccctga tcgcgcctgt acaaataaag caatagcatc acaaatttca      60
caaataaagc attttttttca ctgcc                                           85

<210> SEQ ID NO 50
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
caagtaaagc ggccgcaccg catggcctgg actccgcctg tac                        43

<210> SEQ ID NO 51
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtacaggcgg agtccaggcc atgcggtgcg gccgctttac ttg                        43

<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
caagtaaagc ggccgcacca cttagcctgg actccgcctg tac                        43

<210> SEQ ID NO 53
<211> LENGTH: 43
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 53
gtacaggcgg agtccaggct aagtggtgcg gccgctttac ttg                43

<210> SEQ ID NO 54
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gcaccctgcc gcctggatca agcctgtaca aataaagcaa tagc              44

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ctattgcttt atttgtacag gcttgatcca ggcggcaggg tgcgg             45

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ctagtaccct gccgcctgga ctccgcctgt a                            31

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ctagtaccct gccgccctga tcgcgcctgt a                            31

<210> SEQ ID NO 58
<211> LENGTH: 25
<212> TYPE: DNA
<213> ORGANISM: Homo sapiens

<400> SEQUENCE: 58
gccctgcctt gtccctctca ctccc                                   25

<210> SEQ ID NO 59
<211> LENGTH: 25
<212> TYPE: DNA
<213> ORGANISM: Homo sapiens

<400> SEQUENCE: 59
ggcctgcgtg gactcacagt gcacc                                    25

<210> SEQ ID NO 60
<211> LENGTH: 25
<212> TYPE: DNA
<213> ORGANISM: Homo sapiens

<400> SEQUENCE: 60
accattgtgg tattcacttt cctca                                    25

<210> SEQ ID NO 61
<211> LENGTH: 25
<212> TYPE: DNA
<213> ORGANISM: Homo sapiens

<400> SEQUENCE: 61
accctgccgc ctggactccg cctgt                                    25

<210> SEQ ID NO 62
<211> LENGTH: 25
<212> TYPE: DNA
<213> ORGANISM: Homo sapiens

<400> SEQUENCE: 62
ctactccctg gactagtgca gtcct                                    25

<210> SEQ ID NO 63
<211> LENGTH: 25
<212> TYPE: DNA
<213> ORGANISM: Homo sapiens

<400> SEQUENCE: 63
agcgtctgga cttgtgtaaa cagca                                    25

<210> SEQ ID NO 64
<211> LENGTH: 25
<212> TYPE: DNA
<213> ORGANISM: Homo sapiens

<400> SEQUENCE: 64
gaagcctgtc tctgtacctc taact                                    25

<210> SEQ ID NO 65
<211> LENGTH: 25
<212> TYPE: DNA
<213> ORGANISM: Homo sapiens

<400> SEQUENCE: 65
ccactgcctt tatccaaact taaga                                    25

<210> SEQ ID NO 66
<211> LENGTH: 25
<212> TYPE: DNA
<213> ORGANISM: Homo sapiens

<400> SEQUENCE: 66
accctgcctg tggaggtgac ctgtt                                    25

<210> SEQ ID NO 67
<211> LENGTH: 25
<212> TYPE: DNA
<213> ORGANISM: Homo sapiens

<400> SEQUENCE: 67
ctgccgccgc ctctagagtt actga                                          25

<210> SEQ ID NO 68
<211> LENGTH: 25
<212> TYPE: DNA
<213> ORGANISM: Homo sapiens

<400> SEQUENCE: 68
tgggcgcgag tcgctttgta tcatc                                          25

<210> SEQ ID NO 69
<211> LENGTH: 25
<212> TYPE: DNA
<213> ORGANISM: Homo sapiens

<400> SEQUENCE: 69
acaggtgcct ggagccccg gaacc                                           25

<210> SEQ ID NO 70
<211> LENGTH: 25
<212> TYPE: DNA
<213> ORGANISM: Homo sapiens

<400> SEQUENCE: 70
cagggacgcg ggcccaacaa taaat                                          25

<210> SEQ ID NO 71
<211> LENGTH: 25
<212> TYPE: DNA
<213> ORGANISM: Homo sapiens

<400> SEQUENCE: 71
agggaggctt ggatcagcac ctggg                                          25

<210> SEQ ID NO 72
<211> LENGTH: 25
<212> TYPE: DNA
<213> ORGANISM: Homo sapiens

<400> SEQUENCE: 72
tgctgcccct gctgcccctg ctctg                                          25

<210> SEQ ID NO 73
<211> LENGTH: 25
<212> TYPE: DNA
<213> ORGANISM: Homo sapiens

<400> SEQUENCE: 73
cacccgcctg cccccgcaca agttg                                          25

<210> SEQ ID NO 74
<211> LENGTH: 25
<212> TYPE: DNA
<213> ORGANISM: Homo sapiens

<400> SEQUENCE: 74
accctggacg tgaccgtatc cctct                                          25

<210> SEQ ID NO 75
<211> LENGTH: 25
<212> TYPE: DNA
<213> ORGANISM: Homo sapiens

<400> SEQUENCE: 75
gcccctgcct ggcactgctc accgc                                                25

<210> SEQ ID NO 76
<211> LENGTH: 25
<212> TYPE: DNA
<213> ORGANISM: Homo sapiens

<400> SEQUENCE: 76
agtaaacgaa agtgctgtat gaatt                                                25

<210> SEQ ID NO 77
<211> LENGTH: 25
<212> TYPE: DNA
<213> ORGANISM: Homo sapiens

<400> SEQUENCE: 77
tcctgccgca gacgggcaca gacac                                                25

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: a, c, t, g, unknown or other

<400> SEQUENCE: 78
tgaacccctg cctggaccng cccacctctc                                           30

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
accctgccgc ctggactccg cctgt                                                25

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
accgcatggc ctggactccg cctgt                                                25

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
accacttagc ctggactccg cctgt                                                25

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
accctgccgc ctggactccg cctgt                                        25

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
accctgccgc ctggatcaag cctgt                                        25

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
accctgccgc cctgatcgcg cctgt                                        25

<210> SEQ ID NO 85
<211> LENGTH: 245
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 85
gcggccgcga ctctagatca taatcagcca taccacattt gtagaggttt tacttgcttt    60
aaaaaacctc ccacacctcc ccctgaacct gaaacataaa atgaatgcaa ttgttgttgt   120
taacttgttt attgcagctt ataatggtta caaataaagc aatagcatca caaatttcac   180
aaataaagca ttttttcac tgcattctag ttgtggtttg tccaaactca tcaatgtatc    240
ttaag                                                              245

<210> SEQ ID NO 86
<211> LENGTH: 93
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 86
gcggccgcac cctgccgcct ggactccgcc tgtacaaata aagcaatagc atcacaaatt    60
tcacaaataa agcattttt tcactgcctt aag                                 93

<210> SEQ ID NO 87
<211> LENGTH: 93

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gcggccgcac cgcatggcct ggactccgcc tgtacaaata aagcaatagc atcacaaatt    60
tcacaaataa agcattttt tcactgcctt aag                                  93

<210> SEQ ID NO 88
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gcggccgcac cacttagcct ggactccgcc tgtacaaata aagcaatagc atcacaaatt    60
tcacaaataa agcattttt tcactgcctt aag                                  93

<210> SEQ ID NO 89
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gcggccgcac cctgccgcct ggatcaagcc tgtacaaata aagcaatagc atcacaaatt    60
tcacaaataa agcattttt tcactgcctt aag                                  93

<210> SEQ ID NO 90
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gcggccgcac cctgccgccc tgatcgcgcc tgtacaaata aagcaatagc atcacaaatt    60
tcacaaataa agcattttt tcactgcctt aag                                  93

<210> SEQ ID NO 91
<211> LENGTH: 25
<212> TYPE: RNA
<213> ORGANISM: Homo sapiens

<400> SEQUENCE: 91
acccugccgc cuggacuccg ccugu                                          25

<210> SEQ ID NO 92
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
accgcauggc cuggacuccg ccugu                                          25
```

```
<210> SEQ ID NO 93
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
accacuuagc cuggacuccg ccugu                                            25

<210> SEQ ID NO 94
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
acccugccgc cuggaucaag ccugu                                            25

<210> SEQ ID NO 95
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
acccugccgc ccugaucgcg ccugu                                            25
```